(12) United States Patent
Mizuno et al.

(10) Patent No.: US 7,892,486 B2
(45) Date of Patent: Feb. 22, 2011

(54) METHOD OF STERILIZATION AND APPARATUS THEREFORE

(75) Inventors: Akira Mizuno, (Urbanrafrekanayama1202), 4-2, Kanayama 1-chome, Naka-ku, Nagoya-shi, Aichi (JP) 460-0022; Hiroyuki Yuyama, Toyonaka (JP); Yoshinori Shirahara, Toyonaka (JP)

(73) Assignees: Yuyama Mfg. Co., Ltd., Osaka (JP); Akira Mizuno, Aichi (JP)

( * ) Notice: Subject to any disclaimer, the term of this patent is extended or adjusted under 35 U.S.C. 154(b) by 670 days.

(21) Appl. No.: 10/594,387

(22) PCT Filed: Mar. 29, 2005

(86) PCT No.: PCT/JP2005/005853

§ 371 (c)(1),
(2), (4) Date: Oct. 17, 2006

(87) PCT Pub. No.: WO2005/094907

PCT Pub. Date: Oct. 13, 2005

(65) Prior Publication Data

US 2008/0233002 A1  Sep. 25, 2008

(30) Foreign Application Priority Data

Mar. 31, 2004  (JP) .............................. 2004-104287

(51) Int. Cl.
*A61L 2/20* (2006.01)
(52) U.S. Cl. ....................................................... 422/33
(58) Field of Classification Search ........................ None
See application file for complete search history.

(56) References Cited

U.S. PATENT DOCUMENTS

| | | | |
|---|---|---|---|
| 4,643,876 A | | 2/1987 | Jacobs et al. |
| 4,756,882 A | * | 7/1988 | Jacobs et al. .................. 422/23 |
| 5,084,239 A | | 1/1992 | Moulton et al. |
| 5,876,666 A | * | 3/1999 | Lin et al. ....................... 422/29 |
| 5,951,948 A | * | 9/1999 | Duroselle et al. .............. 422/33 |
| 6,096,266 A | * | 8/2000 | Duroselle ...................... 422/33 |
| 6,224,828 B1 | * | 5/2001 | Lin et al. ....................... 422/33 |
| 6,365,102 B1 | | 4/2002 | Wu et al. |
| 2005/0109739 A1 | * | 5/2005 | Destrez et al. ......... 219/121.54 |

FOREIGN PATENT DOCUMENTS

| | | |
|---|---|---|
| CA | 1 264 217 | 1/1990 |
| CA | 2 302 888 | 9/2000 |
| EP | 0 207 417 | 1/1987 |
| EP | 0 679 407 | 11/1995 |
| EP | 1 040 839 | 10/2000 |
| GB | 2 364 914 | 2/2002 |
| GB | 2 371 986 | 8/2002 |
| JP | 61-293465 | 12/1986 |
| JP | 1-293871 | 11/1989 |
| JP | 2000-308675 | 11/2000 |
| JP | 2002-360672 | 12/2002 |
| JP | 2003-159570 | 6/2003 |
| JP | 2003-250868 | 9/2003 |
| JP | 2003-310720 | 11/2003 |
| JP | 2003-533248 | 11/2003 |
| WO | 01/70281 | 9/2001 |

OTHER PUBLICATIONS

Chinese Office Action (in English language), issued Jul. 4, 2008.

* cited by examiner

*Primary Examiner*—Elizabeth L McKane
(74) *Attorney, Agent, or Firm*—Wenderoth, Lind & Ponack, L.L.P.

(57) ABSTRACT

A harmless sterilization method and sterilization apparatus which provide adequate sterilization effects without residual gas. The method includes a sterilization step in which a chamber containing an object to be sterilized is depressurized; a hydrogen peroxide supply step in which hydrogen peroxide is supplied into the chamber; an ozone supply step in which ozone is supplied into the chamber; a sterilization step in which the hydrogen peroxide and ozone supplied inside the chamber are dispersed to sterilize the object to be sterilized; an exhaust step in which gas inside the chamber is exhausted; and a plasma generation step in which plasma is generated inside the chamber to break down hydrogen peroxide and ozone remaining near the object to be sterilized, and radicals which promote sterilization are generated.

4 Claims, 25 Drawing Sheets

Fig.4
(a)
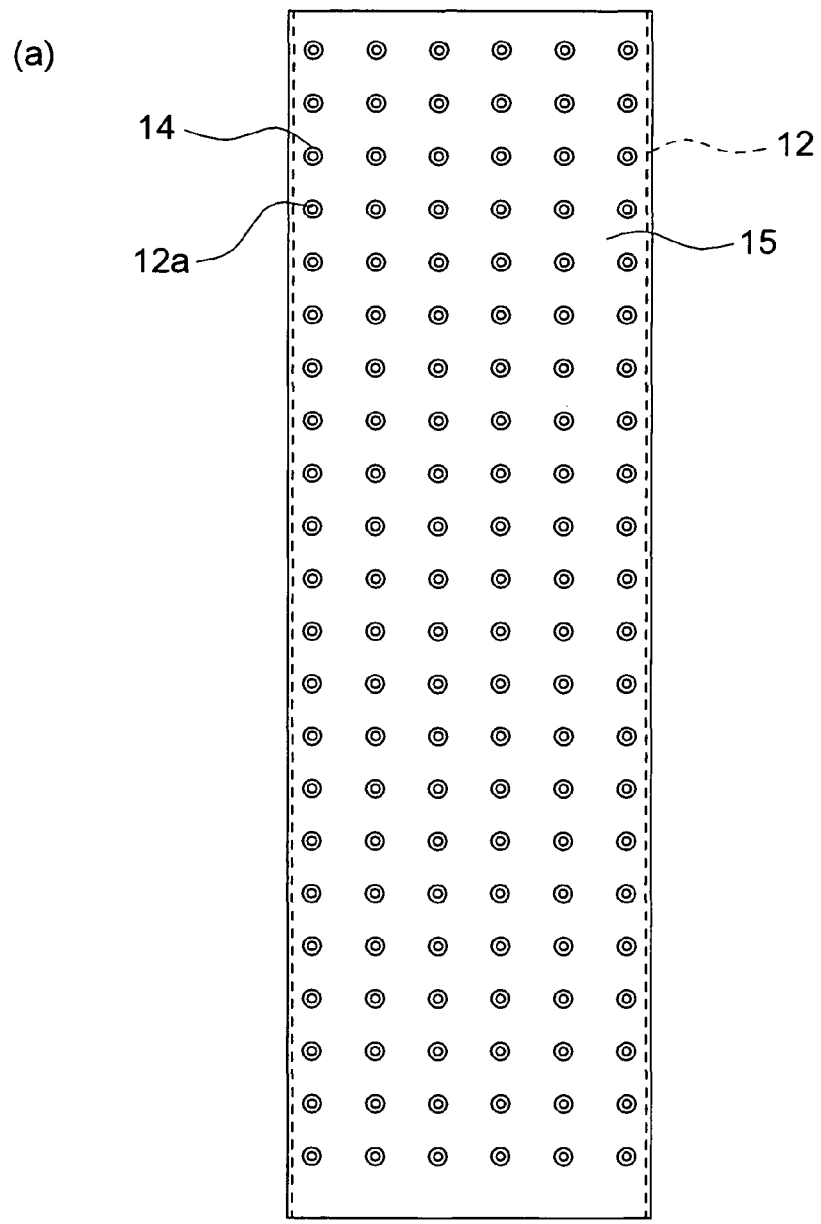
(b)
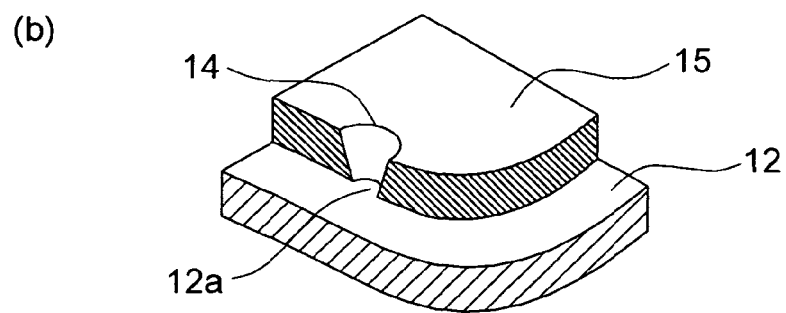

Fig.23
(a)
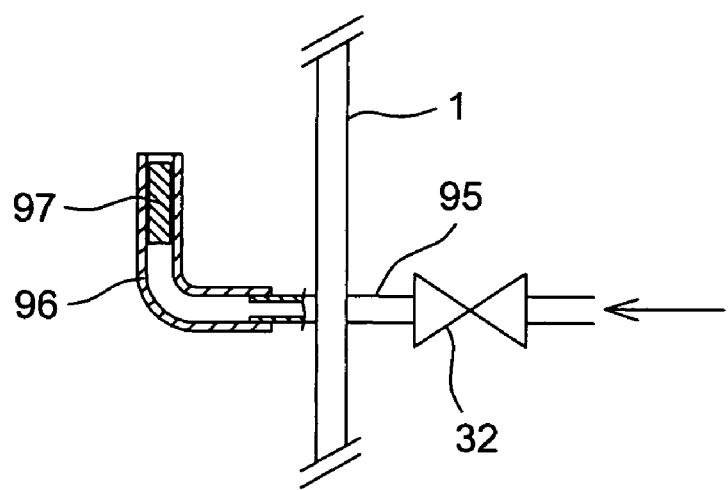
(b)
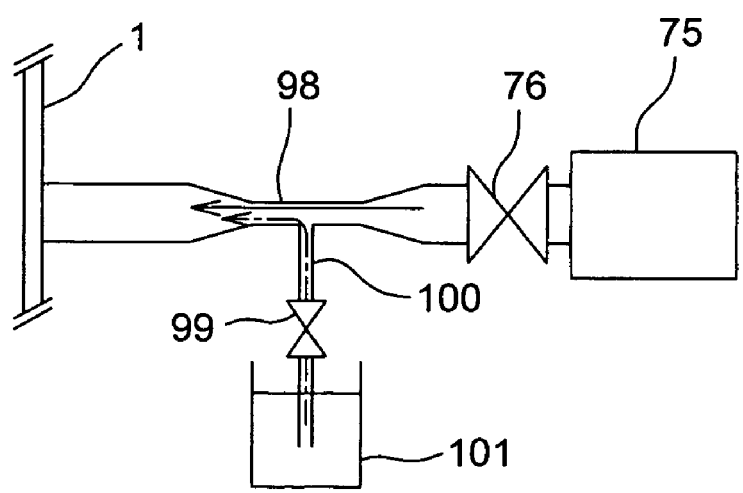

METHOD OF STERILIZATION AND APPARATUS THEREFORE

BACKGROUND OF THE INVENTION

1. Technical Field

The present invention relates to a sterilization method and apparatus for sterilizing medical instruments and the like.

2. Description of the Related Art

Conventional sterilization apparatuses include those combining hydrogen peroxide with plasma, those combining ozone with plasma and those combining hydrogen peroxide with ozone.

As an example of sterilization with hydrogen peroxide plus plasma, JP Laid-open Application No. S61-293465 describes a sterilization method which includes a step of placing an object to be sterilized in a chamber, a step of keeping the object in contact with hydrogen peroxide for a time sufficient for the hydrogen peroxide to become closely involved with the object, a step of generating plasma around the object, and a step of holding the object in the plasma for a time required for sterilization.

JP Laid-open Application No. H1-293871 describes a sterilization method that includes a step of bringing an object to be sterilized into contact with hydrogen peroxide, a step of placing the object including residual hydrogen peroxide in a decompression chamber, a step of generating plasma around the object in the decompression chamber, and a step of holding the object in the plasma for a time sufficient to achieve sterilization by means of active species of the residual hydrogen peroxide.

JP Patent Publication 2003-533248 describes a plasma disinfection system wherein before plasma disinfection liquid hydrogen peroxide is first vaporized, and the hydrogen peroxide in a gaseous state is adjusted to the desired pressure and injected using a flow regulator.

JP Laid-open Application No. 2003-310720 describes a plasma sterilization apparatus provided with a sterilization chamber and a plasma generation chamber which communicates with the sterilization chamber so that plasma generated in the plasma generation chamber is supplied together with a sterilization agent to the sterilization chamber.

As an example of sterilization with ozone plus plasma, JP Laid-open Application No. 2003-159570 describes a sterilization and dry washing apparatus wherein oxygen or a mixed gas containing oxygen is subjected to discharge excitation within a treatment chamber housing an object to be treated to generate plasma, gaseous water molecules are sprayed, and the gas is exposed to ultraviolet rays.

JP Laid-open Application No. 2003-250868 describes a plasma sterilization processor wherein oxygen or a gas containing oxygen within a gas supply pipe is converted to plasma and supplied to a sterilization chamber, a gas supplied within the sterilization chamber is also converted to plasma, and these plasmas are contained by a magnet arranged within the sterilization chamber.

As an example of sterilization with hydrogen peroxide plus ozone, JP Laid-open Application No. 2002-360672 describes a sterilizer wherein hydrogen peroxide is first supplied to a treatment container which houses an object to be sterilized, and ozone is then added to the treatment container.

However, although all these conventional sterilization apparatuses are constructed so as not to leave residual harmful gas, their sterilization effects have not been adequate. The problem is that when the concentration of the sterilizing agent is raised to improve the sterilization effects, gas remains in the chamber after sterilization, and more time is required for breaking down the residual gas (aeration).

SUMMARY OF THE INVENTION

In light of the aforementioned problems of prior art, it is an object of the present invention to provide a harmless sterilization method and apparatus capable of providing adequate sterilization effects without leaving residual gas. Another object is to provide a sterilization method and apparatus capable of shortening the sterilization time.

To solve the aforementioned problems, the sterilization method of the present invention comprises:

a decompression step of decompressing a chamber which houses an object to be sterilized;

a hydrogen peroxide supply step of supplying hydrogen peroxide into the aforementioned chamber;

an ozone supply step of supplying ozone into the aforementioned chamber; a sterilization step of sterilizing the object to be sterilized by diffusing the hydrogen peroxide and ozone supplied within the aforementioned chamber;

an exhaust step of exhausting the gas from within the aforementioned chamber; and a plasma generation step of generating plasma within the aforementioned chamber.

The sterilization method of the present invention first sterilizes an object to be sterilized by means of hydrogen peroxide which has been supplied and vaporized within a chamber, and then sterilizes the object to be sterilized by means of ozone supplied within the chamber. Once the gas within the chamber has been exhausted, the hydrogen peroxide and ozone remaining near the object to be sterilized are broken down by means of plasma generated within the chamber, generating radicals that promote sterilization. This method is thus harmless because the hydrogen peroxide and ozone remaining near the object to be sterilized are broken down.

The aforementioned exhaust step preferably comprises a decomposition step in which the gas being exhausted from the aforementioned chamber is broken down into oxygen and water. This is harmless because the residual gas is broken down into oxygen and water, and the chamber can be immediately used again once sterilization is complete. Alternatively, a decomposition step can be included in which the ozone in the gas being exhausted from the aforementioned chamber is broken down.

The aforementioned sterilization step preferably comprises a step of circulating sterilization gas in the aforementioned chamber. In this way the sterilization gas in the chamber can be dispersed uniformly, enhancing the sterilization effects.

Moreover, the sterilization apparatus of the present invention comprises:

a chamber capable of housing an object to be sterilized;

a decompression unit for decompressing the inside of the chamber;

a hydrogen peroxide supply unit for supplying hydrogen peroxide into the chamber;

an ozone supply unit for supplying ozone into the chamber;

an exhaust unit for exhausting gas from within the chamber; and a plasma generation unit for generating plasma within the chamber.

In the sterilization apparatus of the present invention, an object to be sterilized is sterilized through the combined use of hydrogen peroxide, ozone and plasma. Moreover, not only is residual hydrogen peroxide near the object to be sterilized broken down, but sterilization of the object to be sterilized is also promoted by the various radicals produced during decomposition.

The aforementioned hydrogen peroxide supply unit preferably comprises an antiscattering member to prevent the hydrogen peroxide supplied in liquid form to the inside of the aforementioned chamber from scattering. In this way, scattering due to rapid evaporation is prevented when the hydrogen peroxide is supplied in a liquid state within the decompressed chamber.

The aforementioned exhaust unit preferably has a residual gas decomposition unit that breaks down gas exhausted from the aforementioned chamber into oxygen and water. The residual gas is broken down into oxygen and water, making the system harmless so that the chamber can be immediately used again after sterilization is complete. An ozone decomposition catalyst for breaking down the ozone in the gas being exhausted from the aforementioned chamber can be included in place of this decomposition unit.

It is desirable to further include a sterilization gas circulation unit that circulates the sterilization gas in the aforementioned chamber. It is thus possible to uniformly disperse the sterilization gas in the chamber, thereby enhancing the sterilization effects.

The aforementioned plasma generator preferably has a high-voltage electrode and a low-voltage electrode within the aforementioned chamber, with either one of the aforementioned high-voltage electrode and low-voltage electrode comprising a plurality of point electrodes surrounded by an insulator. This makes it possible to generate a uniform plasma by means of interference among the discharge spaces generated by multiple point electrodes. The aforementioned high-voltage electrode is preferably connected to a high-voltage power source, while the low-voltage electrode is grounded.

EFFECT OF THE INVENTION

Greater sterilization effects are produced by the sterilization method and apparatus of the present invention through the combined use of hydrogen peroxide, ozone and plasma. Moreover, not only is the residual hydrogen peroxide near the object to be sterilized broken down, but sterilization of the object to be sterilized is further promoted by the various radicals generated during decomposition, thereby greatly shortening the sterilization time.

BRIEF DESCRIPTION OF THE DRAWINGS

FIG. 4(a) is a bottom view of a high-voltage electrode;
FIG. 4(b) is a perspective view of the perforated part of an insulating body;
FIG. 23(a) shows another embodiment of a hydrogen peroxide supply unit;
FIG. 23(b) shows yet another embodiment of a hydrogen peroxide supply unit.

Figure 1:
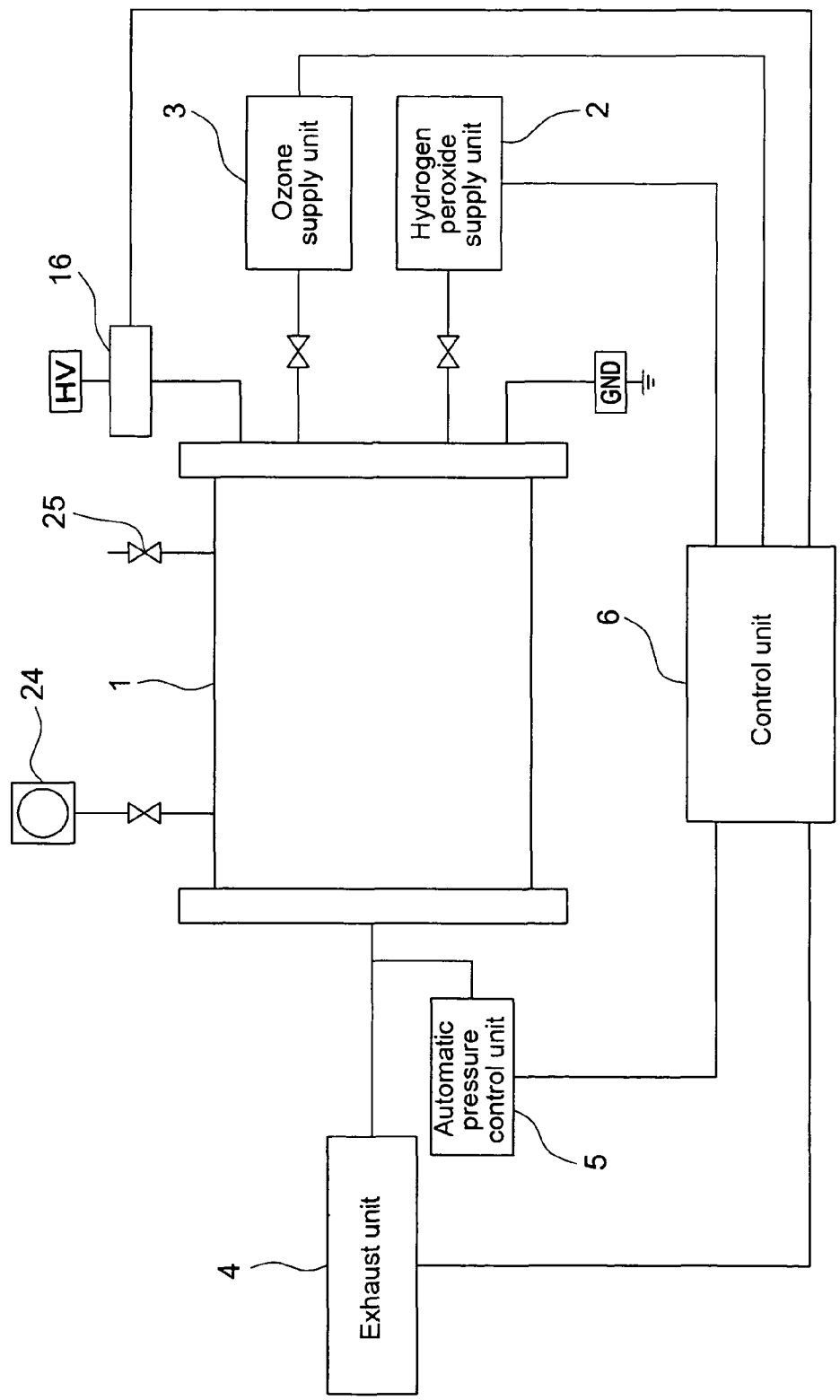
FIG. 1 is a schematic block diagram of a sterilization apparatus according to a first embodiment of the present invention.

EXPLANATION OF REFERENCE NUMERALS 1 chamber
1A sterilization gas circulation unit
2, 2A hydrogen peroxide supply unit
3, 3A ozone supply unit
4, 4A exhaust unit
12 high-voltage electrode
12a point electrodes
13 low-voltage electrode
15 dielectric
16 plasma generator
20 glass wool (antiscattering member)
50 vacuum pump
52 gas decomposition mechanism
87 ozone decomposition catalyst

DETAILED DESCRIPTION OF THE INVENTION

Embodiments of the present invention are explained below with reference to the accompanying drawings.

FIG. 1 shows a sterilization apparatus according to the first embodiment of the present invention. This sterilization apparatus comprises chamber 1, hydrogen peroxide supply unit 2, ozone supply unit 3, exhaust unit 4, automatic pressure control unit 5, and control unit 6.

Figure 2:
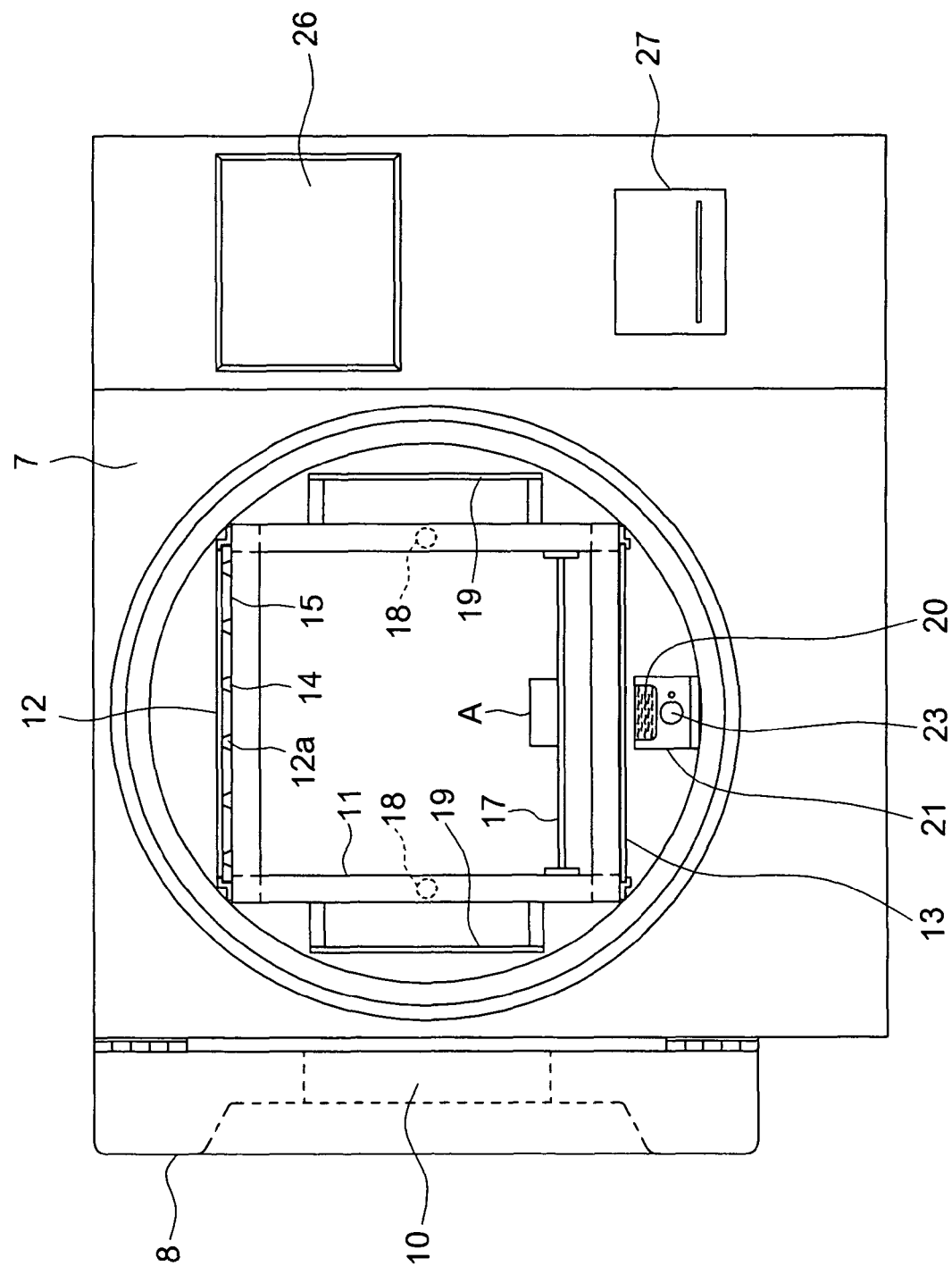
FIG. 2 is a front view showing a sterilization apparatus of the present invention with the door open.
Figure 3:
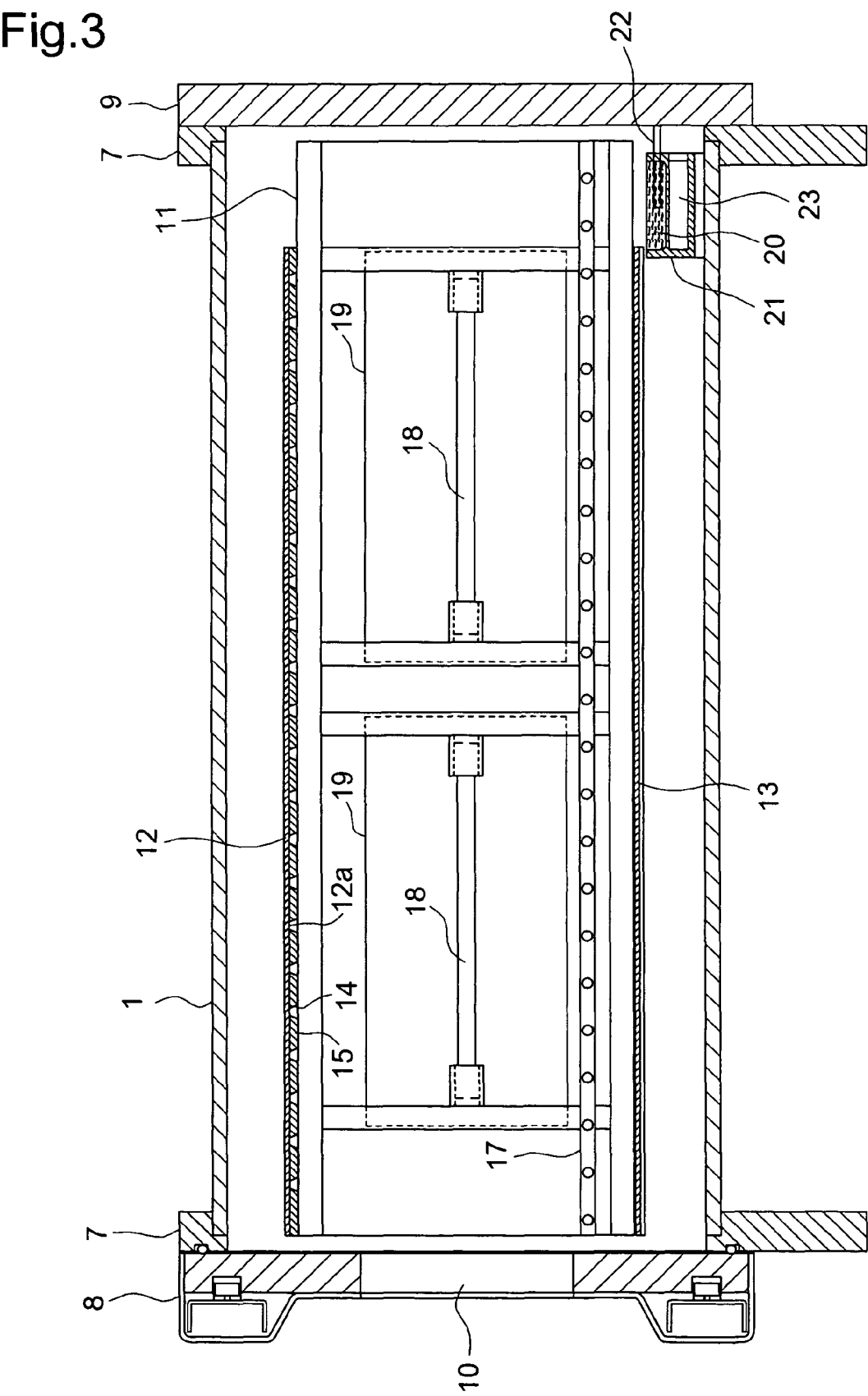
FIG. 3 is a side cross-section of the sterilization apparatus of FIG. 2.

Chamber 1 has the cylindrical shape as shown in FIGS. 2 and 3, with flanges 7 attached to both ends. Door 8 is attached to the front flange 7 so as to open and close freely. Closed cover 9 is attached to the back flange 7. Door 8 is equipped with glass window 10, which allows the interior to be checked visually.

Chamber 1 contains frame 11, with rectangular high-voltage electrode 12 and low-voltage electrode 13 arranged on the top and bottom of frame 11. Dielectric 15 (insulating body) with holes 14 formed therein (5 mm in diameter in this embodiment a fixed pitch (20 mm to 100 mm) as shown in FIG. 4 is affixed to the surface of high-voltage electrode 12 which faces low-voltage electrode 13. The part exposed through holes 14 constitutes point electrodes 12a. Instead of high-voltage electrode 12 being made into point electrodes 12a in this way, however, low-voltage electrode 13 could be made into point electrodes. As shown in FIG. 1, high-voltage electrode 12 is connected to high-voltage power source HV via plasma generator 16 so that the discharge maintenance voltage is 1100V, while low-voltage electrode 13 is grounded. Voltage applied by high-voltage power source HV may be either direct voltage or alternating voltage. The plasma generated by plasma generator 16 may be of any kind, but is preferably high-frequency discharge plasma which has been discharged in high frequencies of MHz or more, or microwave plasma which has been discharged in the microwave range ($10^3$ to $10^4$ MHz). Shelf 17 consisting of multiple rods arranged at fixed intervals is attached between the left and right sides of frame 11. The object to be sterilized A is placed on shelf 17. Infrared heaters 18 are attached to both sides of frame 11. Behind the heaters are attached protective plates 19 for protecting chamber 1 from heat from infrared heaters 18. Chamber 1 also contains hydrogen peroxide evaporation plate 21, which is filled with glass wool 20. Hydrogen peroxide injection pipe 22 is inserted into glass wool 20 inside this evaporation plate 21. Cartridge heater 23 for promoting vaporization of hydrogen peroxide is provided below glass wool 20.

As shown in FIG. 1, pressure gauge 24 for detecting the pressure in chamber 1 and suction valve 25 for releasing chamber 1 into the atmosphere are attached to the outside of chamber 1. As shown in FIG. 2, control panel 26 for displaying the pressure, temperature, sterilization processes and the like inside chamber 1 and carrying out various operations and settings and journal printer 27 for printing the displays of control panel 26 on roll paper as necessary are provided on the side of door 8 of chamber 1.

Figure 5:
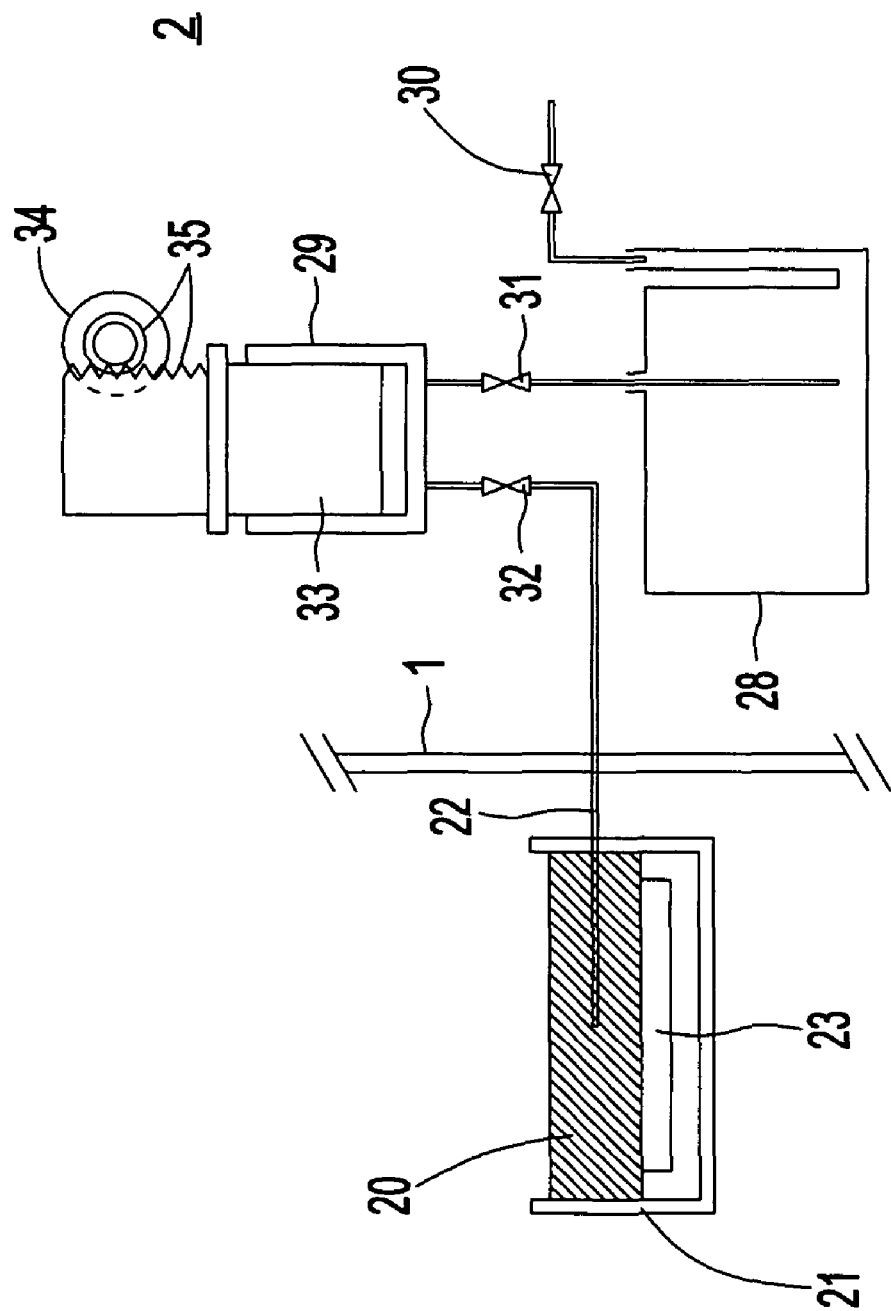
FIG. 5 is a block diagram of a hydrogen peroxide supply unit.

As shown in FIG. 5, hydrogen peroxide supply unit 2 comprises hydrogen peroxide tank 28 and cylinder 29. Hydrogen peroxide tank 28 can be opened to the atmosphere via electromagnetic valve 30. Cylinder 29 is connected to hydrogen peroxide tank 28 via electromagnetic valve 31, and is connected to hydrogen peroxide injection pipe 22 of the aforementioned chamber 1 via electromagnetic valve 32. Piston 33, which fits inside cylinder 29, reciprocates by means of push motor 34 via rack and pinion mechanism 35, sucking about 3 cc of hydrogen peroxide from hydrogen peroxide tank 28 into cylinder 29 and forcing it into glass wool 20 via hydrogen peroxide supply pipe 22 of chamber 1.

Figure 6:
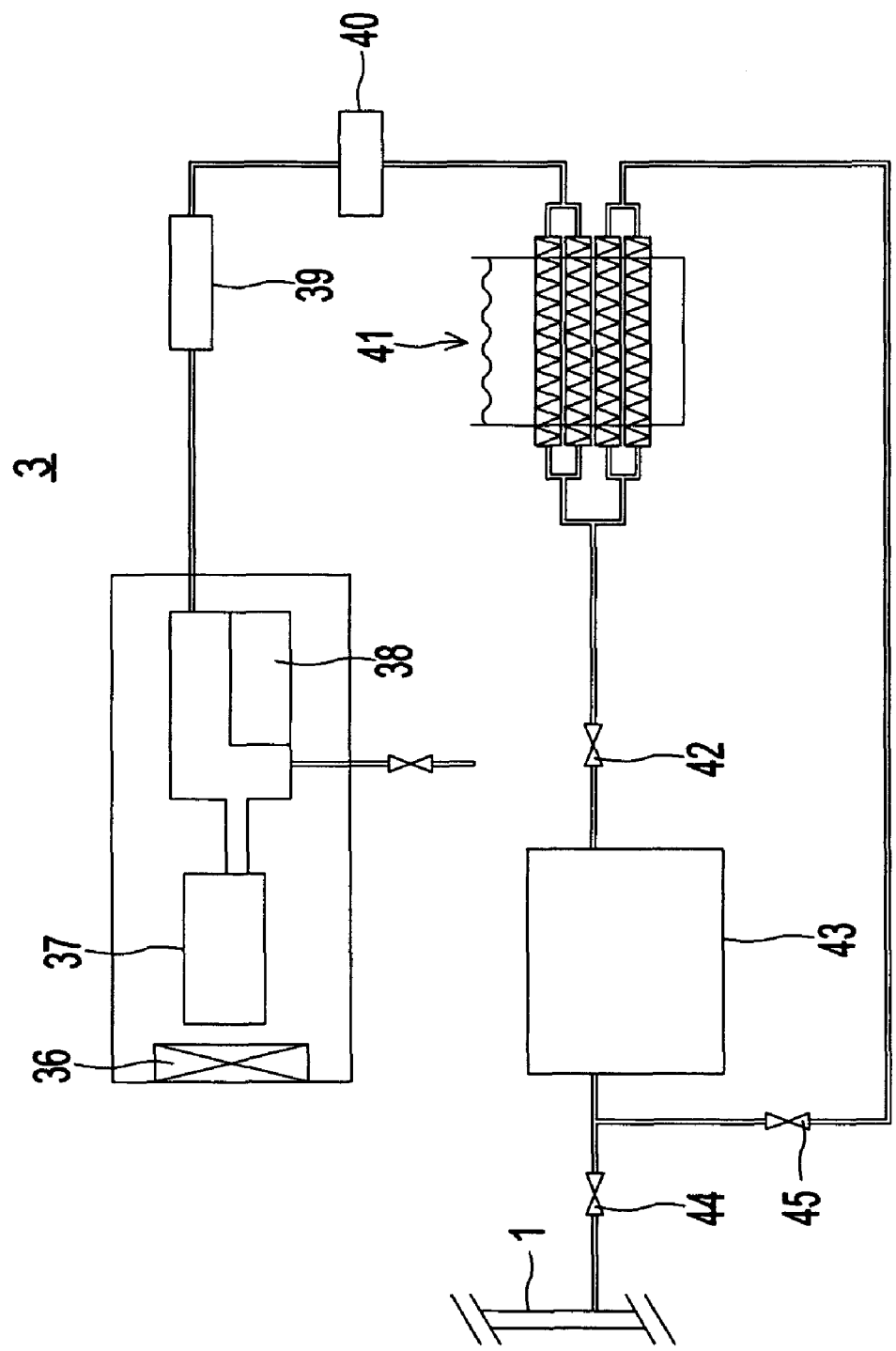
FIG. 6 is a block diagram of an ozone supply unit.

As shown in FIG. 6, in ozone supply unit 3 air with a high oxygen concentration of 30% is produced when air sucked in by fan 36 is passed through oxygen enrichment membrane 37 and cooled by Peltier element 38. This high-oxygen-concentration air is passed through filter 39 and supplied by pump 40 to ozone generator 41. In the ozone generator, ozone is generated and accumulated in ozone tank 43 via electromagnetic valve 42 so that ozone is supplied to chamber 1 via electromagnetic valve 44. The ozone in ozone tank 43 can be returned to ozone generator 41 via electromagnetic valve 45 as necessary.

Figure 7:
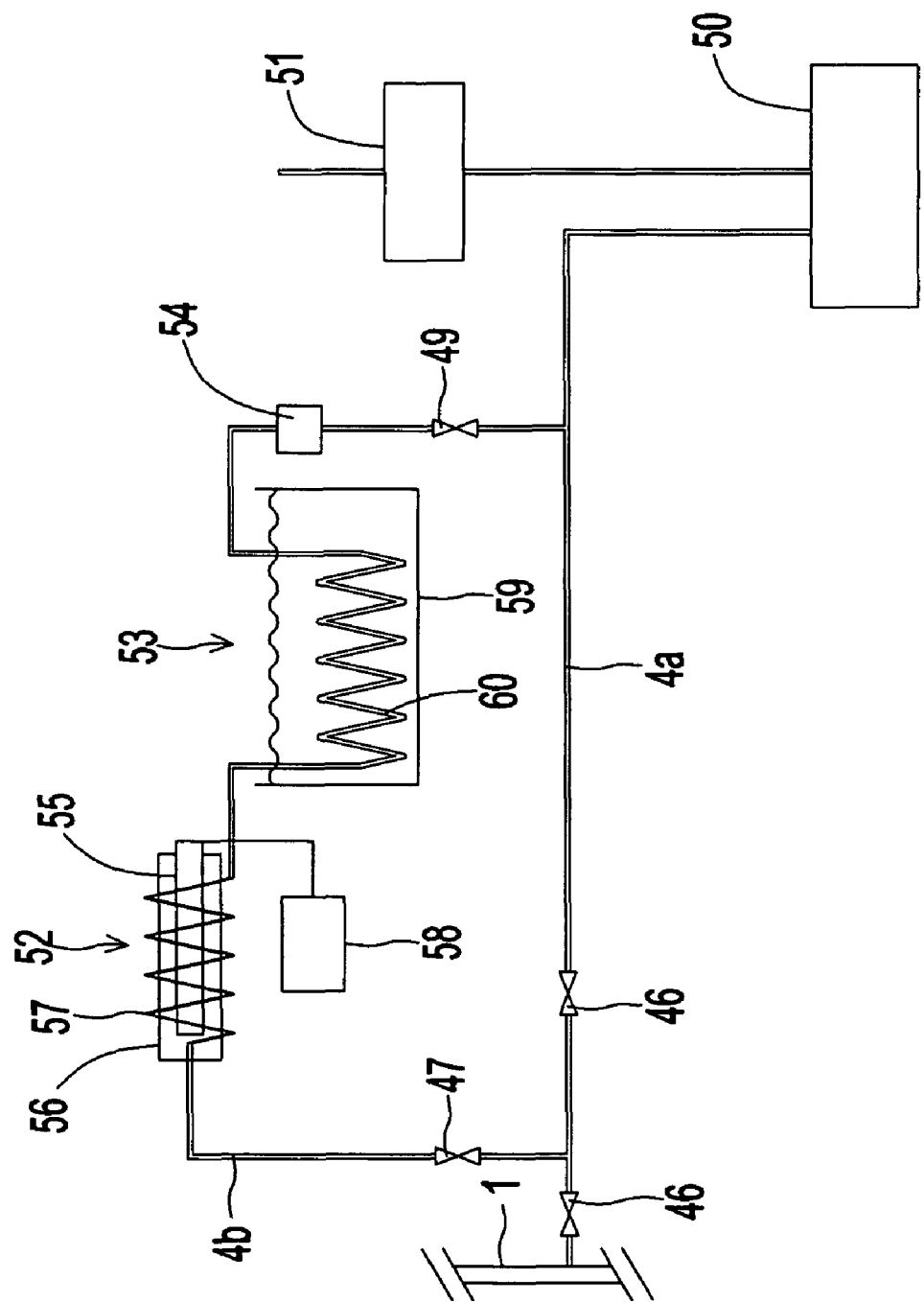
FIG. 7 is a block diagram of an exhaust unit.

As shown in FIG. 7, exhaust unit 4 has exhaust line 4a, which connects to chamber 1, and gas decomposition line 4b, which branches from the upstream end of exhaust line 4a and rejoins exhaust line 4a downstream. Exhaust line 4a and gas decomposition line 4b have electromagnetic valves 46 and 47, respectively, downstream from the branching point. Gas decomposition line 4b has electromagnetic valve 49 upstream from the rejoining point. Vacuum pump 50 and oil mist separator 51 are provided downstream from electromagnetic valve 48 of exhaust line 4a. Gas decomposition mechanism 52, cooling mechanism 53 and drain separator 54 are provided in upstream-to-downstream order between electromagnetic valves 47 and 49 of gas decomposition line 4b. In gas decomposition mechanism 52, stainless pipe 57 is arranged on the outside of aluminum tube 56, which contains heater 55, and this stainless pipe 57 communicates with gas decomposition line 4b. Heater 55 adjusts the temperature of the ozone and the hydrogen peroxide flowing through stainless pipe 57 to 200° C. by means of temperature controller 58. Cooling mechanism 53 has stainless pipe 60 arranged in water tank 59, which contains water, with stainless pipe 60 communicating with gas decomposition line 4b.

Automatic pressure control unit 5 drives vacuum pump 50 of the aforementioned exhaust unit 4 based on the pressure detected by pressure gauge 24, controlling the pressure inside chamber 1 at a fixed pressure.

Control unit 6 controls infrared heaters 18 and 23 in the aforementioned chamber 1, plasma generator 16, hydrogen peroxide supply unit 2, ozone supply unit 3, exhaust unit 4, automatic pressure control unit 5 and the like.

Operation of the sterilization apparatus of the first embodiment with the aforementioned configuration will be explained below.

Figure 8:
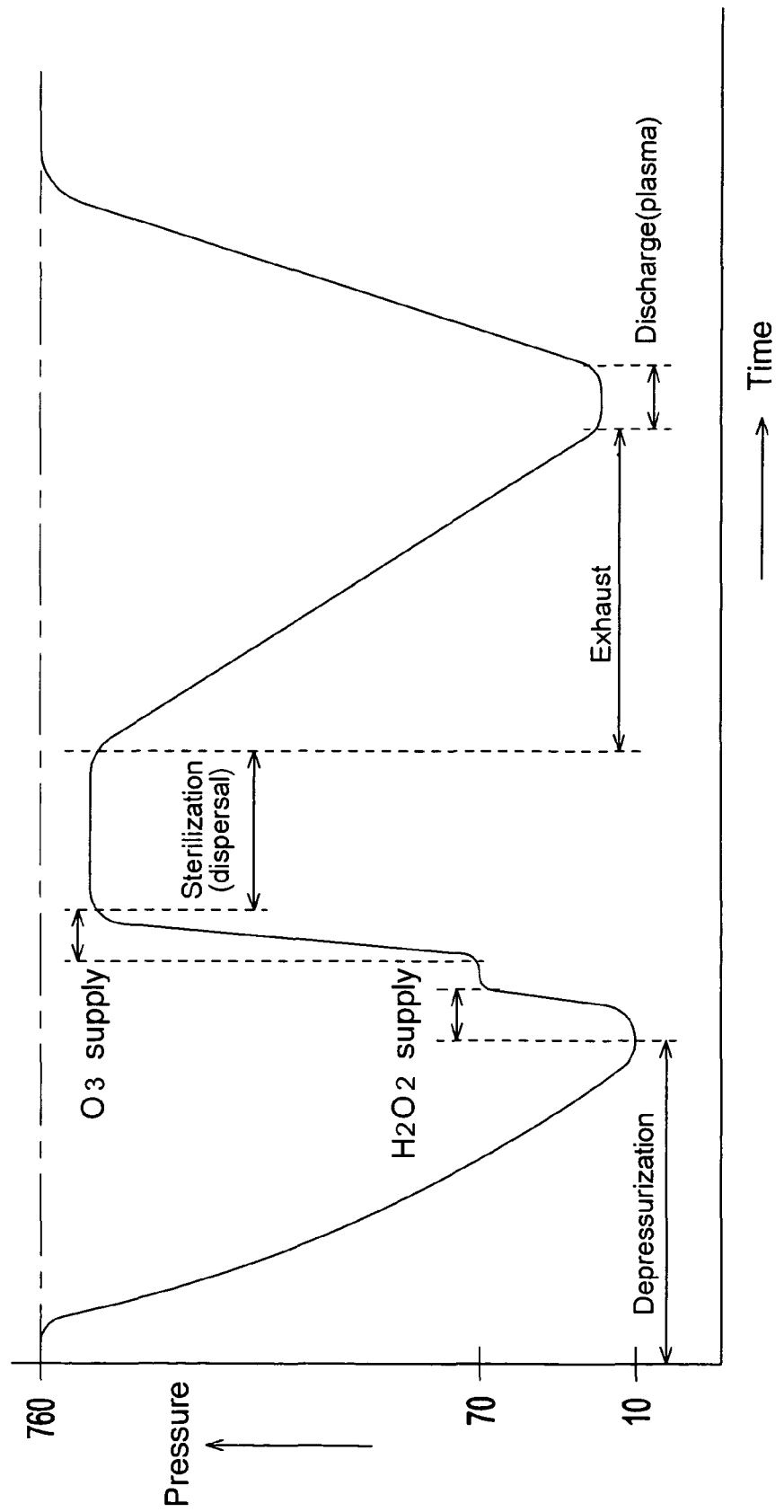
FIG. 8 shows pressure changes within a chamber.

Object A to be sterilized is placed on shelf 17 in chamber 1. Infrared heater 18 is turned on to adjust the inside of chamber 1 to a fixed temperature while at the same time vacuum pump 50 of exhaust unit 4 is driven to reduce the pressure inside chamber 1 to about 10 Torr (1333.2 Pa) as shown in FIG. 8. Since air is present in chamber 1 during this depressurization, it is exhausted via exhaust line 4a without passing through gas decomposition line 4b within exhaust unit 4. Next, piston 33 of hydrogen peroxide supply unit 2 is driven to supply hydrogen peroxide inside chamber 1. The hydrogen peroxide vaporizes as soon as it reaches the inside of depressurized chamber 1. Scattering of the hydrogen peroxide as it vaporizes is prevented because the hydrogen peroxide is forced into glass wool 20 through hydrogen peroxide supply pipe 22. Vaporization of the hydrogen peroxide is also promoted by cartridge heater 23 at the bottom of glass wool 20.

A specific time after the pressure inside chamber 1 has risen to about 70 Torr (9332.5 Pa) due to the supply of hydrogen peroxide, electromagnetic valve 44 of ozone supply unit 3 is opened to supply ozone stored in ozone tank 43 to the inside of chamber 1. Once the pressure inside chamber 1 has risen to atmospheric pressure or less (such as around 700 Torr (93325 Pa)) due to the supply of ozone, this state is maintained for a fixed period of time so that the hydrogen peroxide and ozone disperse inside chamber 1, sterilizing the object to be sterilized.

The hydrogen peroxide supplied to chamber 1 acts on the object to be sterilized as an oxidant. Water and oxygen are produced by this sterilization process as shown by equation 1 below.

[Equation 1]

The ozone supplied inside chamber 1 also acts on the object to be sterilized as an oxidant. Oxygen and oxygen ions are produced by this sterilization process as shown by equation 2 below.

[Equation 2]

Moreover, hydrogen peroxide and ozone react inside chamber 1 to produce water and oxygen as shown by equation 3 below.

[Equation 3]

Next, infrared heater 18 is turned off, and vacuum pump 50 of exhaust unit 4 is driven again to exhaust the gas from inside chamber 1. Since the gas exhausted here contains hydrogen peroxide and ozone, it is exhausted through gas decomposition line 4b without passing through exhaust line 4a inside exhaust unit 4. Hydrogen peroxide and ozone conducted to gas decomposition mechanism 52 of gas decomposition line 4a are heated to 200° C. and broken down into water and oxygen as shown by equation 3 above, then cooled by cooling mechanism 53 and exhausted harmlessly via vacuum pump 50 and oil mist separator 51.

When infrared heater 18 is turned off the temperature inside chamber 1 falls to about 40° C., causing the hydrogen peroxide to condense and adhere to the object to be sterilized A. When the pressure inside chamber 1 is lowered to about 1 Torr (133.32 Pa), plasma is generated for a fixed amount of time within chamber 1 by plasma generator 16. When plasma is generated in a hydrogen peroxide and ozone atmosphere, superoxides are produced by the reaction of oxygen and electrons as shown by equation 4 below. These superoxides react with water to produce active oxygen species (hydroxy radicals). The object to be sterilized is further sterilized by these hydroxy radicals. Since high-voltage electrode 12 in chamber 1 forms multiple point electrodes 12a, a uniform plasma discharge is generated between each point electrode 12a and low-voltage electrode 13. As a result, the sterilizing effect is uniform for all objects to be sterilized A inside chamber 1. Moreover, because high-frequency voltage is applied as mentioned above by high-voltage power source HV, it is easier to maintain discharge because the starting voltage is lower, allowing a highly uniform plasma to be produced. As a result, more radicals can be produced inside chamber 1, and greater sterilization effects can be expected.

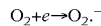

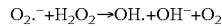 [Equation 4]

At this stage, because the hydrogen peroxide and ozone inside chamber 1 are exhausted in the aforementioned exhaust step and broken down by gas decomposition mechanism 52, the aforementioned reaction is attributed to a reaction by the hydrogen peroxide and ozone remaining near object A to be sterilized. Consequently, sterilization is further promoted because sterilization by hydrogen peroxide and ozone is followed by further sterilization by radicals generated through plasma discharge.

Once sterilization by plasma discharge is complete, suction valve 25 is opened, opening the inside of chamber 1 to the atmosphere. Since the aforementioned radicals convert instantly to oxygen and water as soon as plasma discharge is stopped, this is harmless because no harmful gas remains in chamber 1 after sterilization. The sterilization step described above takes about 1 hour from beginning of depressurization to release to atmosphere.

The inventors performed experiments to evaluate sterilization by the sterilization method of the present invention. *Bacillus subtilis* was used as the biological indicator. Using the following procedures, only *Bacillus subtilis* spores were allowed to survive on polypropylene sheets to serve as the samples.

(1) *Bacillus subtilis* are pre-cultured for 24 hours in an incubator at 35° C. using standard agar medium.

(2) Following the pre-culture, *Bacillus subtilis* are uniformly inoculated in a roux jar using a heat-treated platinum loop (single colony).

(3) This is cultured (smear culture) for 7 days at 35° C. in a 500 ml roux jar using an incubator.

(4) The cultured cells are sampled, and a sporulation rate of 80% is confirmed under a microscope.

(5) 20 glass beads and 20 ml of sterile water are added to the roux jar, and the roux jar is tilted backwards and forwards and right and left to detach the spores from the surface of the medium.

(6) The resulting spore liquid is filtered with sterile gauze, and the medium components and spores are separated by centrifugation.

(7) The spore liquid is heated at 80° C. for 10 minutes to destroy vegetative cells.

(8) The spore suspension is transferred to a triangular flask, and stored in a refrigerator at 5° C.

(9) The spore concentration of the spore suspension is measured (standard plate count).

(10) The bacterial liquid is dripped onto sterile-treated specimen film to a spore concentration of $10^6$ CFU/0.1 ml.

(11) This is dried overnight at room temperature.

(12) After being dried, the specimen is placed in a sterile plate and stored in a refrigerator at 5° C.

Samples prepared by the aforementioned procedures were placed in chamber 1, and sterilized under 4 sets of conditions: with only hydrogen peroxide supplied, with only ozone supplied, with only plasma discharged, and with plasma hydrogen peroxide and ozone supplied followed by plasma discharge according to the invention of this application. Under each set of conditions, the number of cells (CFU) was measured by a standard plate count before sterilization and after sterilization.

Figure 9:
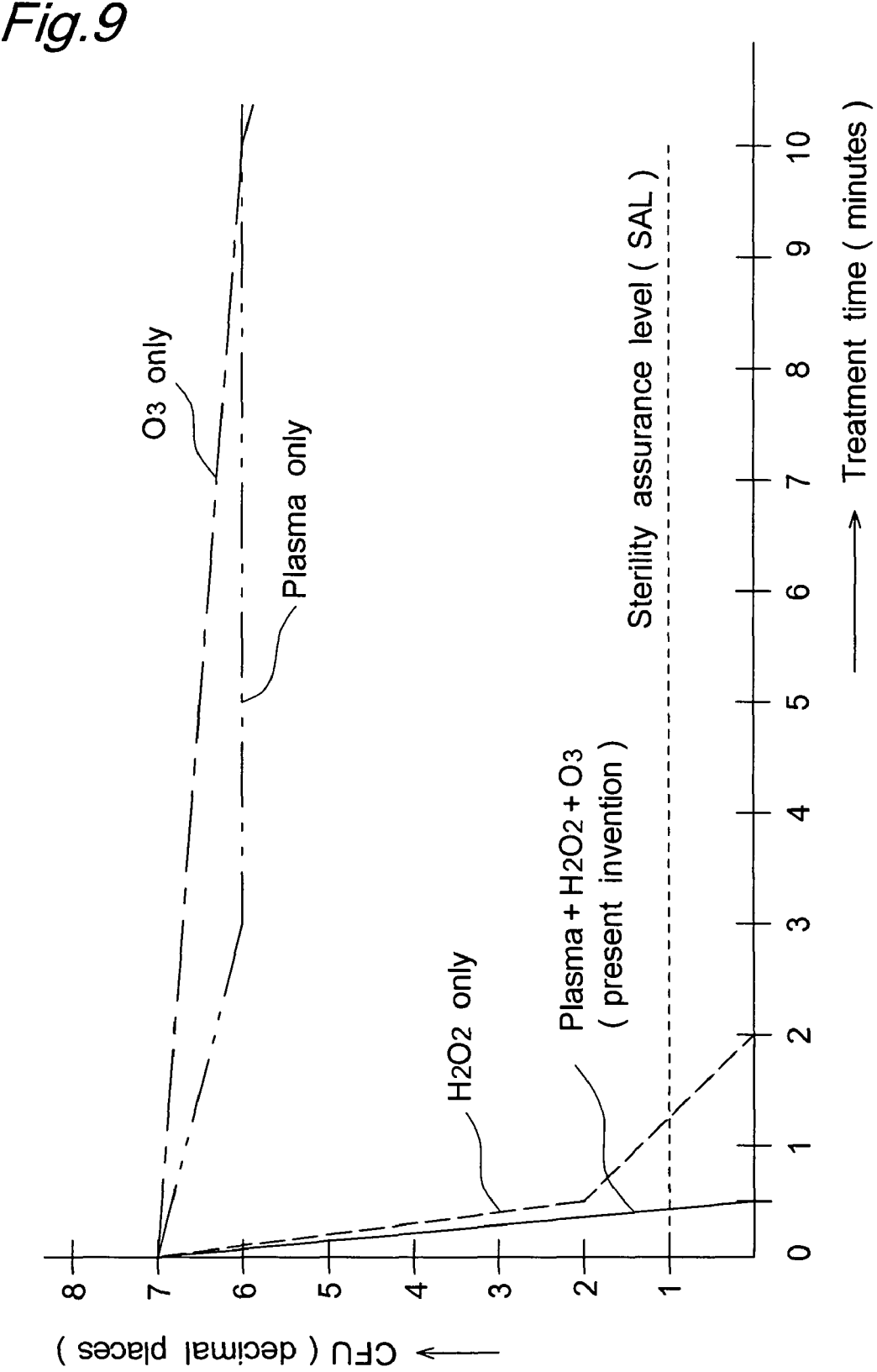
FIG. 9 shows sterilization speeds under various conditions.

FIG. 9 shows changes over time in the sterilization rate or in other words in the digit number of the cell count under the aforementioned 4 sets of conditions. The decrease in digits was calculated according to equation 5 below.

Decrease in digits=log(count before sterilization [CFU]/count after sterilization [CFU])     [Equation 5]

The time taken for the count to decrease by one digit is given as D. D value is calculated according to equation 6 below and used to indicate the sterilization effect. The treatment time here includes hydrogen peroxide injection and dispersion, ozone injection and dispersion and plasma discharge but not the time taken to decompress or exhaust chamber 1.

D [sec/digit]=treatment time [sec]/decrease in digits [digit]     [Equation 6]

As shown in FIG. 9, it took 10 minutes for the cell count to fall from 7 to 6 digits under conditions of ozone sterilization only, giving a D value of 600 [sec/digit]. With plasma sterilization only it took 3 minutes for the cell count to fall from 7 to 6 digits, giving a D value of 180 [sec/digit]. With hydrogen peroxide sterilization only, it took 30 seconds for the cell count to fall from 7 to 2 digits, for a D value of 30/(7−2)=6 [sec/digit]. Under the conditions of the present invention in which hydrogen peroxide and ozone were supplied followed by plasma discharge, it took 30 seconds for the cell count to fall from 7 to 0 digits, for a D value of 30/(7−0)=4.3 [sec/digit]. That is, in the present invention the D value is much smaller, indicating a much stronger sterilization effect than is obtained with either ozone sterilization, hydrogen peroxide sterilization or plasma sterilization by itself. As shown in FIG. 9, in the present invention the sterilization rate was extremely fast, with a level below the sterility assurance level (SAL) being reached in only 30 seconds or less.

Figure 10:
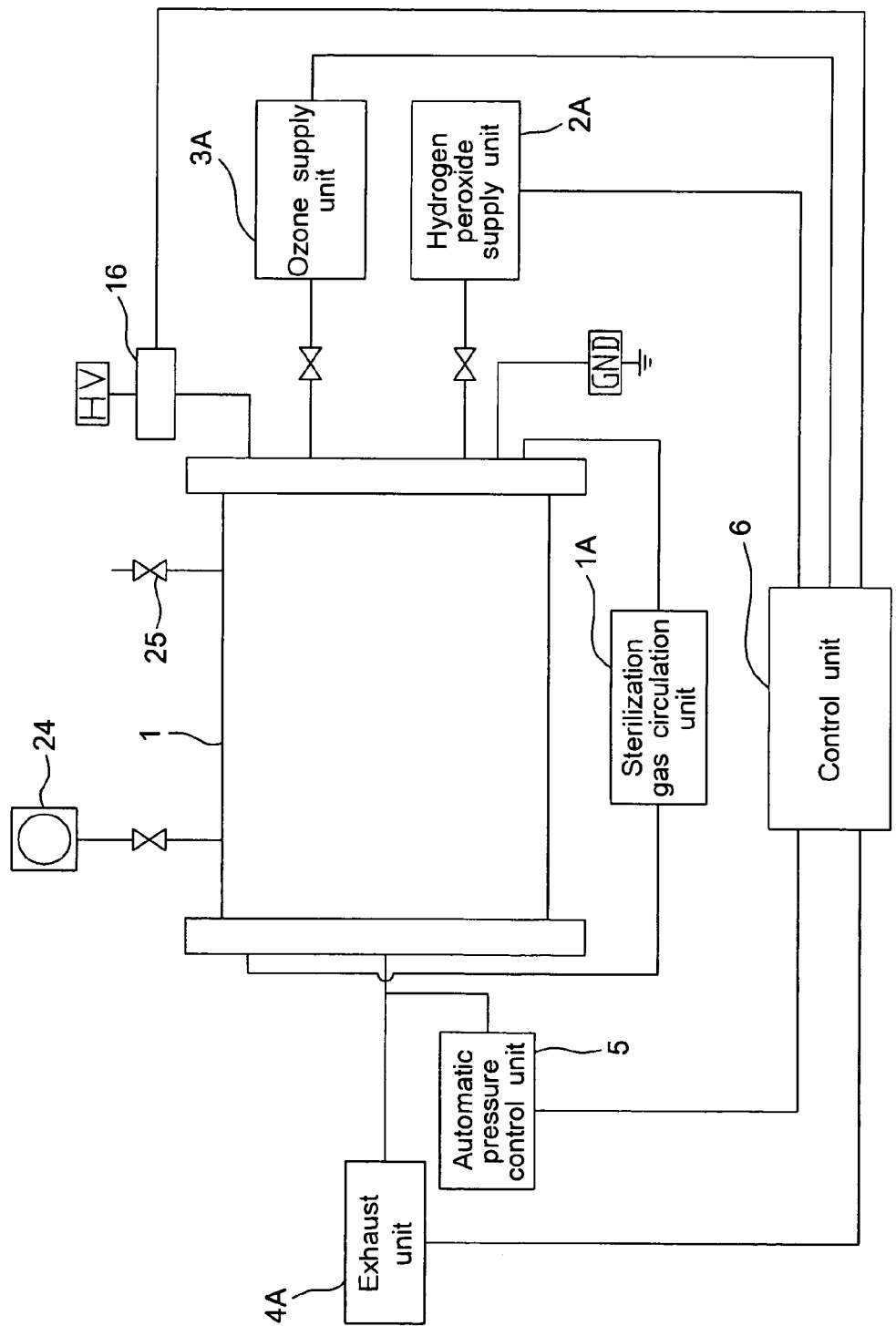
FIG. 10 is a schematic block diagram of a sterilization apparatus according to a second embodiment of the present invention.

FIG. 10 shows a sterilization apparatus according to the second embodiment of the present invention. This sterilization apparatus has hydrogen peroxide supply unit 2A, ozone supply unit 3A and exhaust unit 4A in place of the hydrogen peroxide supply unit 2, ozone supply unit 3 and exhaust unit 4 of the aforementioned first embodiment shown in FIG. 1, and also has sterilization gas circulation unit 1A. Since it is otherwise identical to the first embodiment the corresponding parts are indicated with the same symbols and are not explained.

Figure 11:
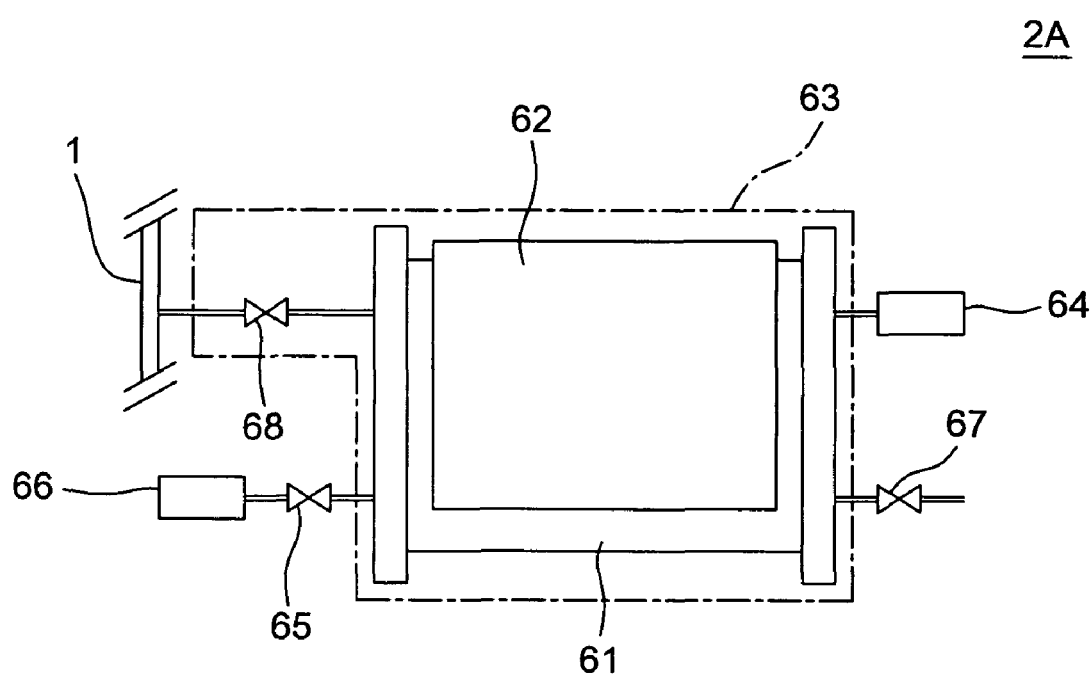
FIG. 11 is a block diagram of a hydrogen peroxide supply unit.

As shown in FIG. 11, hydrogen peroxide supply unit 2A has hydrogen peroxide vaporization chamber 61. Hydrogen peroxide vaporization chamber 61 is equipped with a heater 62 such as a silicon rubber heater wrapped around the outside thereof, and is covered overall by heat insulator 63. Pressure sensor 64 is attached to hydrogen peroxide vaporization chamber 61, to which vacuum pump 66 is also connected via electromagnetic valve 65, allowing the inside of the chamber to be depressurized. Moreover, hydrogen peroxide vaporization chamber 61 is connected to a hydrogen peroxide source (not shown) via electromagnetic valve 67, and to chamber 1 via electromagnetic valve 68.

Figure 12:
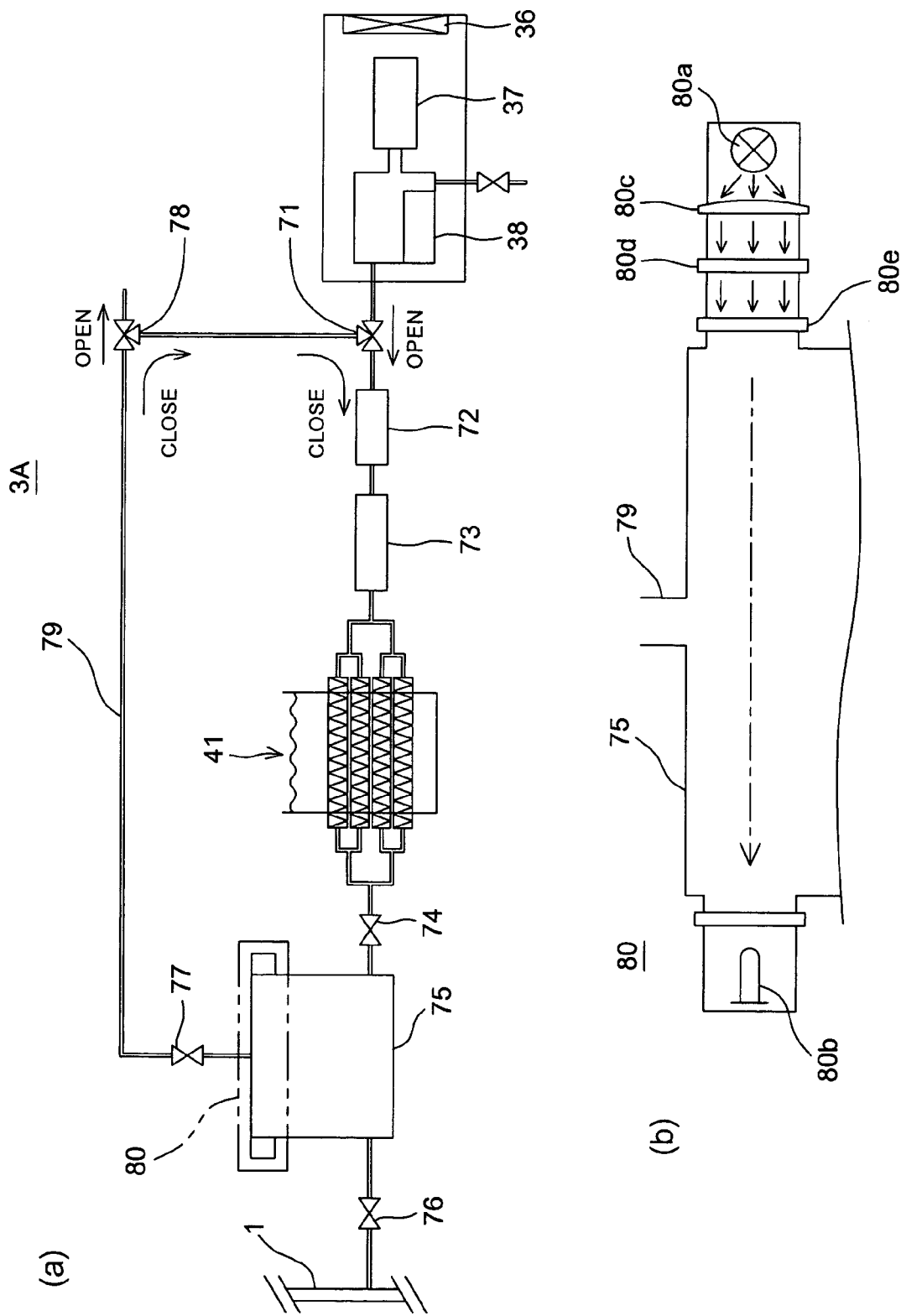
FIG. 12(a) is a block diagram of an ozone supply unit.
FIG. 12(b) is a diagram of an ozone concentration meter.

As shown in FIG. 12($a$), ozone supply unit 3A has an oxygen enrichment part as in the aforementioned first embodiment comprising fan 36, oxygen enrichment membrane 37 and Peltier element 38. High-oxygen-content air that has been enriched by the oxygen enrichment part is sucked into pump 72 via first three-way valve 71, and supplied to ozone generator 41 via silica gel or other filter 73. The ozone generated by ozone generator 41 is accumulated in ozone tank 75 via electromagnetic valve 74. The ozone in ozone tank 74 is supplied to the inside of chamber 1 via electromagnetic valve 76. Ozone tank 75 is connected, via circulation line 79 having electromagnetic valve 77 and second three-way valve 78, to first three-way valve 71 on the inlet side of the aforementioned pump 72. The third opening of second three-way valve 78 on circulation line 79 is open to the atmosphere.

Ozone tank 75 is equipped with ozone concentration meter 80 for detecting the ozone concentration inside ozone tank 75. As shown in FIG. 12($b$), this ozone concentration meter comprises UV lamp 80$a$ and photodiode 80$b$, which are attached to opposite walls of ozone tank 75, along with a concentration detection circuit (not shown). The light from UV lamp 80$a$ passes through collimator lens 80$c$, visible light filter 80$d$ and quartz glass 80$e$ to illuminate the inside of ozone tank 75 as ultraviolet light. Some of the ultraviolet rays passing through ozone tank 75 are absorbed by the ozone, and the remainder are received by photodiode 80$b$. The amount of light received by photodiode 80$b$ is converted to ozone concentration by the concentration detection circuit (not shown). The ozone inside ozone tank 75 continues to be returned to the inlet side of pump 72 via circulation line 79 until the ozone concentration detected by the aforementioned ozone concentration meter 80 reaches a specific value.

Figure 13:
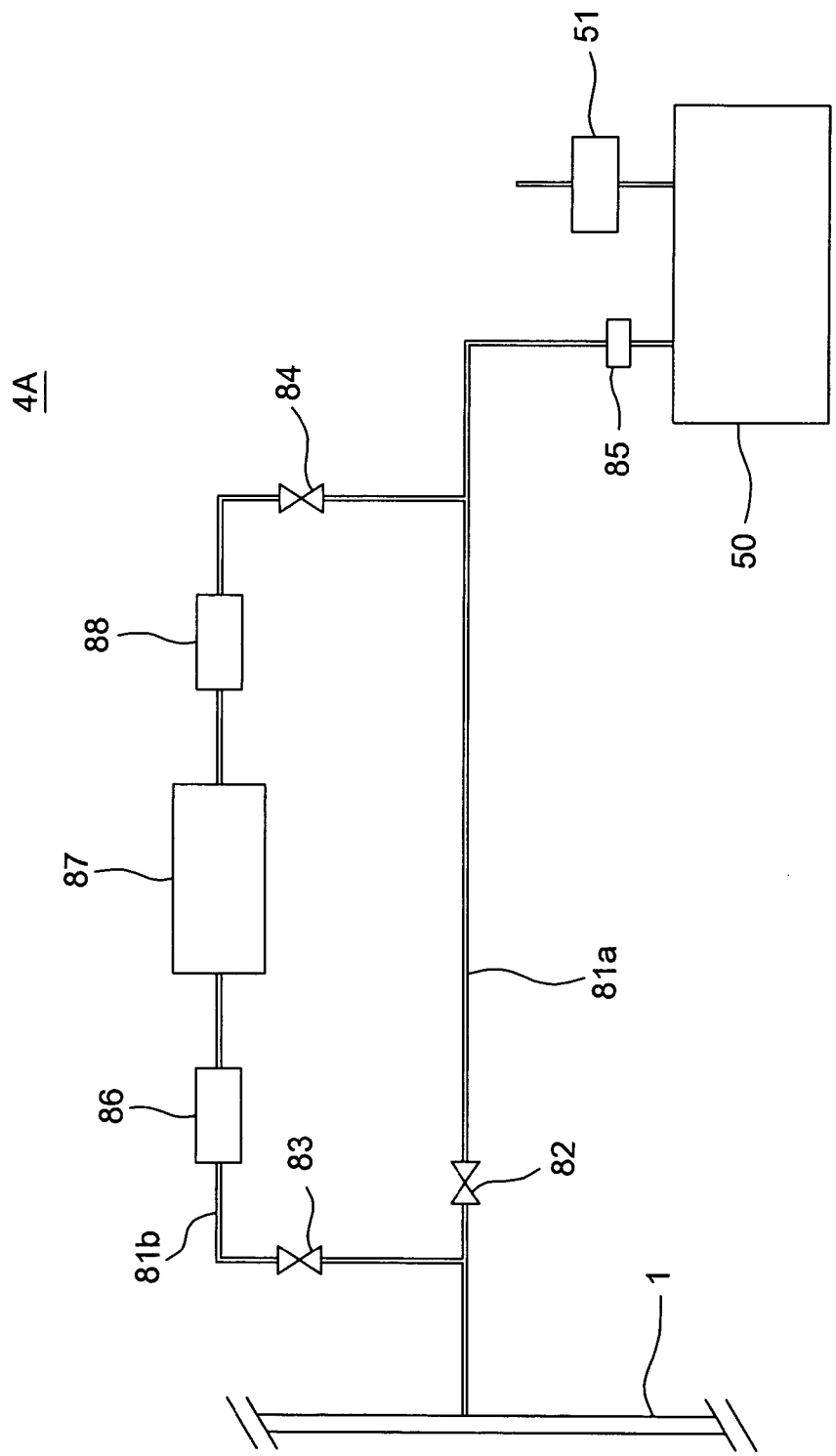
FIG. 13 is a block diagram of an exhaust unit.
Figure 14:
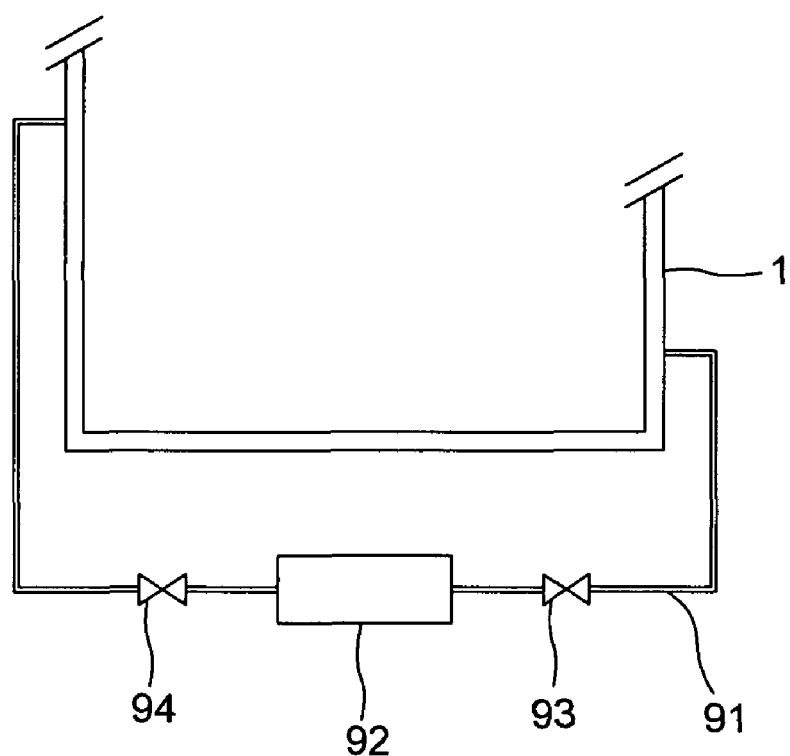
FIG. 14 is a block diagram of a sterilization gas circulation unit.

As shown in FIG. 13, exhaust unit 4A has exhaust line 81$a$, which is connected to chamber 1, and gas decomposition line 81$b$, which branches from the upstream part of exhaust line 81$a$ and rejoins exhaust line 81$a$ downstream. Exhaust line 81$a$ and gas decomposition line 81$b$ are equipped with electromagnetic valves 82 and 83, respectively, downstream from the branch point. Gas decomposition line 81$b$ is also equipped with electromagnetic valve 84 upstream from the joining point. Exhaust line 81$a$ is equipped with ozone concentration meter 85, vacuum pump 50 and oil mist separator 51 in that order moving downstream from the joining point with gas decomposition line 81$b$, and is open to the atmosphere. Gas decomposition line 81$b$ is provided with silica gel or other drying agent 86, ozone decomposition catalyst 87, and active carbon or other hydrogen peroxide adsorption agent 88 in that order starting from upstream.

Sterilization gas circulation unit 1A comprises sterilization gas circulation line 91, which is connected between one end and the other of chamber 1, circulation pump 92 on sterilization gas circulation line 91, and electromagnetic valves 93 and 94 on the inlet and outlet sides of circulation pump 92, so that driving circulation pump 92 circulates sterilization gas inside chamber 1, bringing it into full contact with the object to be sterilized.

Operation of sterilization apparatus of the second embodiment having the above configuration will be explained with reference to the flow chart of FIG. 15 and the pressure change diagram of FIG. 16.

Exhaust unit 4A is operated in Step S101 to depressurize chamber 1. When the pressure inside chamber 1 has reached a specific pressure such as 3.8 Torr (500 Pa) for example in Step S102, hydrogen peroxide supply unit 2A is operated to supply hydrogen peroxide inside chamber 1 in Step S103. Once the pressure inside chamber 1 has risen to a specific pressure such as 22.6 Torr (3013 Pa) for example due to the supply of hydrogen peroxide, ozone supply unit 3A is operated in Step S104 to supply ozone inside chamber 1. Once the pressure inside chamber 1 has risen to about 700 Torr (93325 Pa) for example due to the supply of ozone, this state is maintained for a specific time in Step S105 to disperse the sterilization gas inside chamber 1 and sterilize the object to be sterilized (main sterilization step). Sterilization gas circulation unit 1A is operated here to circulate the sterilization gas inside chamber 1. Once the main sterilization step is complete, exhaust unit 4A is operated in Step S106 to exhaust and break down the gas inside chamber 1. Once the pressure has reached a specific pressure such as 3.8 Torr (500 Pa) for example in Step S107 due to the exhaustion of gas from inside chamber 1, exhaust unit 4A is once again operated in Step S108 to depressurize chamber 1. Once the pressure inside chamber 1 has reached a specific pressure such as 1.0 Torr (133 Pa) for example in Step S109, plasma is generated for a fixed time in chamber 1 by plasma generator 16 in Step S110 to sterilize the object to be sterilized (sub-sterilization step). Once the sub-sterilization step is complete, suction valve 25 is opened in Step S111 to open chamber 1 to the atmosphere.

Figure 17:
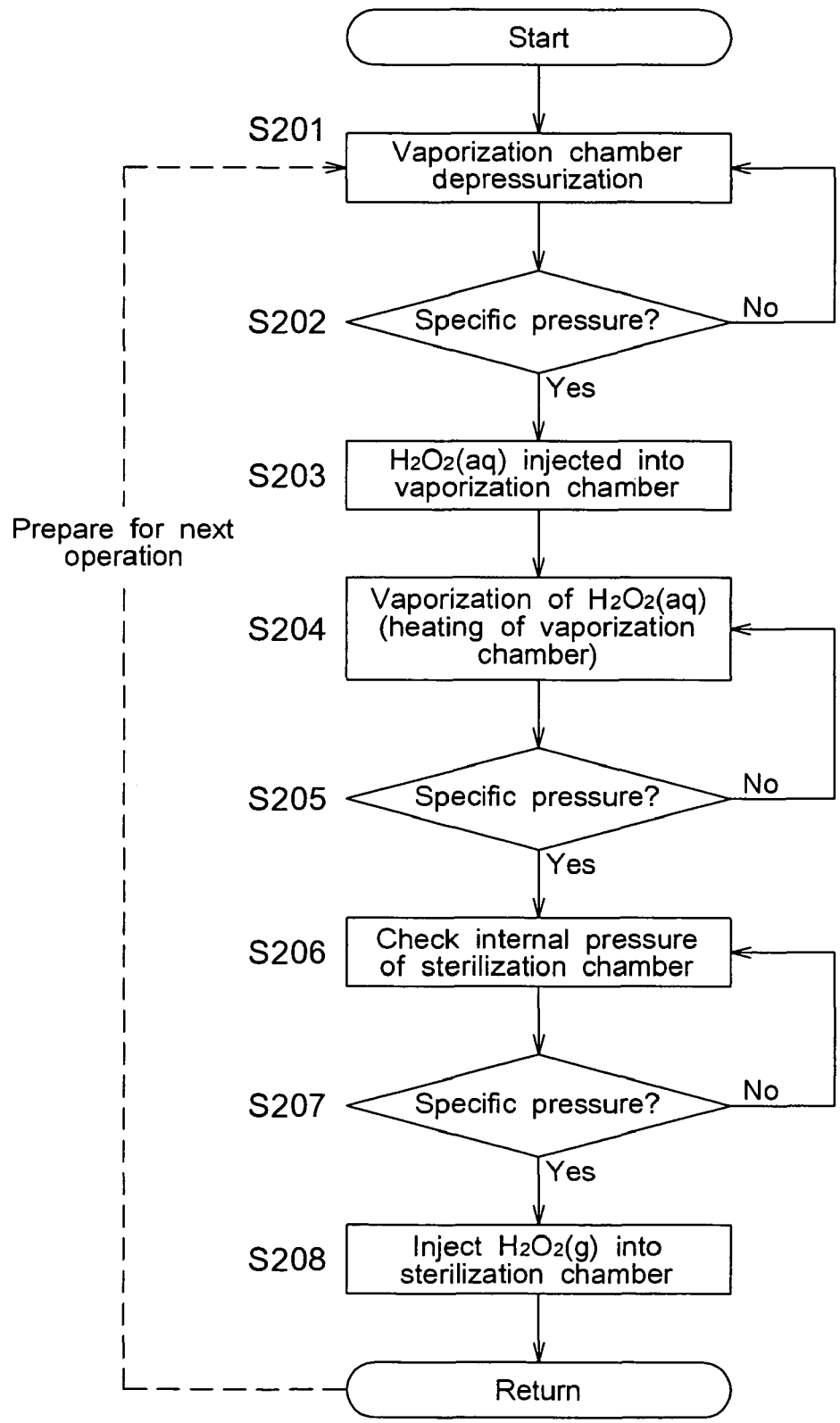
FIG. 17 is a flow chart of a hydrogen peroxide supply step.
Figure 18:
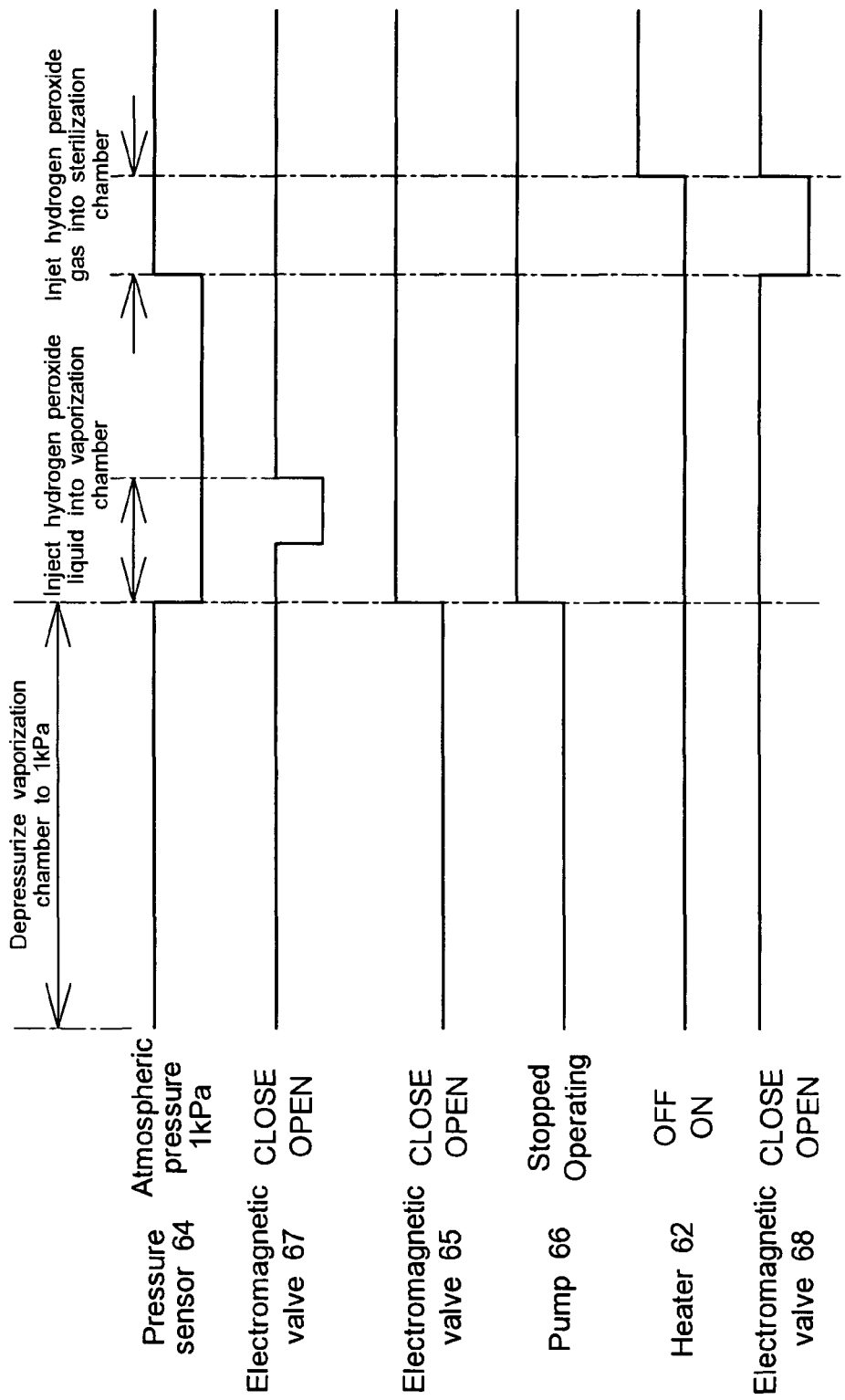
FIG. 18 is a time chart of a hydrogen peroxide supply step.

The hydrogen peroxide supply step of Step S103 is explained in detail using the flow chart of FIG. 17 and the time chart of FIG. 18. First, in Step S201, heater 62 is turned on, electromagnetic valve 65 is opened and pump 66 is driven to depressurize hydrogen peroxide vaporization chamber 61. Once the pressure inside hydrogen peroxide vaporization chamber 61 has reached a specific pressure such as 7.5 Torr (1 kPa) for example in Step S202, electromagnetic valve 65 is closed, pump 66 is stopped and electromagnetic valve 67 is then opened in Step S203 to inject hydrogen peroxide into hydrogen peroxide vaporization chamber 61. Hydrogen peroxide vaporization chamber 61 is heated by heat from heater 62 in Step S204 to vaporize the hydrogen peroxide. Once the pressure inside hydrogen peroxide vaporization chamber 61 has reached a specific pressure such as positive pressure or once the pressure has ceased to rise in Step S205 due to vaporization of hydrogen peroxide, the pressure inside chamber 1 is checked in Step S206. If the pressure inside chamber 1 is a specific pressure such as 3.8 Torr (500 Pa) for example in Step S207, electromagnetic valve 67 is closed and electromagnetic valve 68 is opened for a specific time in Step S208 to inject the vaporized hydrogen peroxide into chamber 1. Once hydrogen peroxide injection is complete, go to Step 201 to prepare for the next hydrogen peroxide injection if there is to be more than one sterilization, but if not, go to Return to move on to the next step (ozone supply step).

Figure 19:
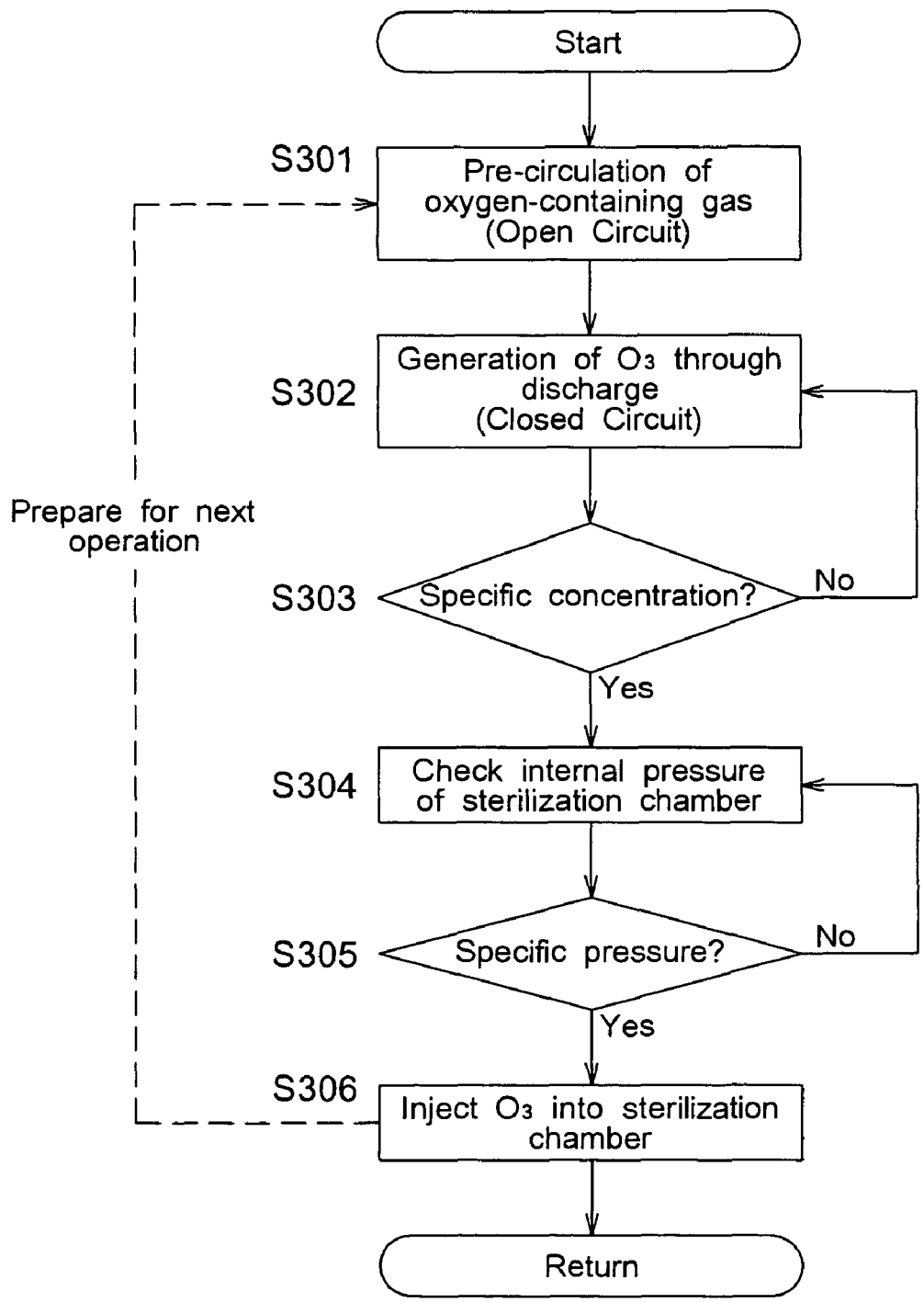
FIG. 19 is a flow chart of an ozone supply step.
Figure 20:
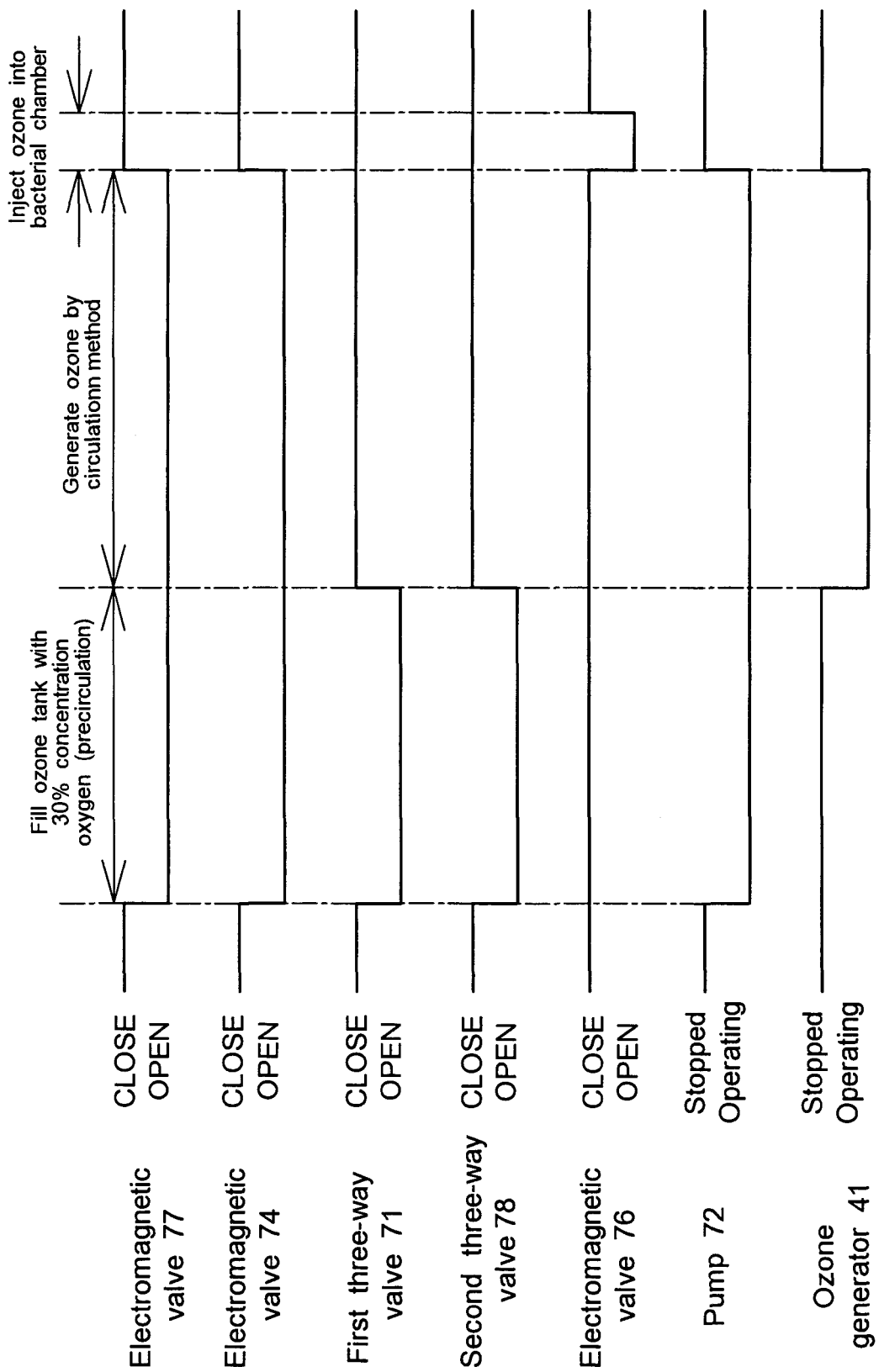
FIG. 20 is a time chart of an ozone supply step.

The ozone supply step of Step S104 is explained in detail using the flow chart of FIG. 19 and the time chart of FIG. 20. First, ozone generator 41 is stopped, electromagnetic valves 74 and 77 are opened, and first three-way valve 71 and second three-way valve 78 are switched to the open direction ("OPEN" in the figure) in step S301 to make circulation line 79 an open circuit. Pump 72 is driven to bring oxygen-containing gas from the oxygen enrichment part to ozone tank 75, and circulation line 79 is opened to the atmosphere to perform pre-circulation. Next, in Step S302, first three-way valve 71 and second three-way valve 78 are switched to the closed direction ("CLOSED") in the figure, making circulation line 79 a closed circuit, and ozone generator 41 is operated to generate ozone. Once the ozone concentration in ozone tank 75 has reached a specific concentration such as 6000 ppm for example as indicated by ozone concentration meter 80 in Step S303, the pressure inside chamber 1 is confirmed in Step S304. If the pressure inside chamber 1 is a specific pressure such as 22.6 Torr (3013 Pa) for example in Step S306, pump 72 and ozone generator 41 are stopped and electromagnetic valves 74 and 77 are closed, after which electromagnetic valve 76 is opened for a specific period of time to inject ozone into chamber 1. Once ozone injection is complete, return to Step S301 to prepare for the next ozone if there is to be more than one sterilization, or if not, go to Return to move on to the next step (main sterilization step).

Figure 21:
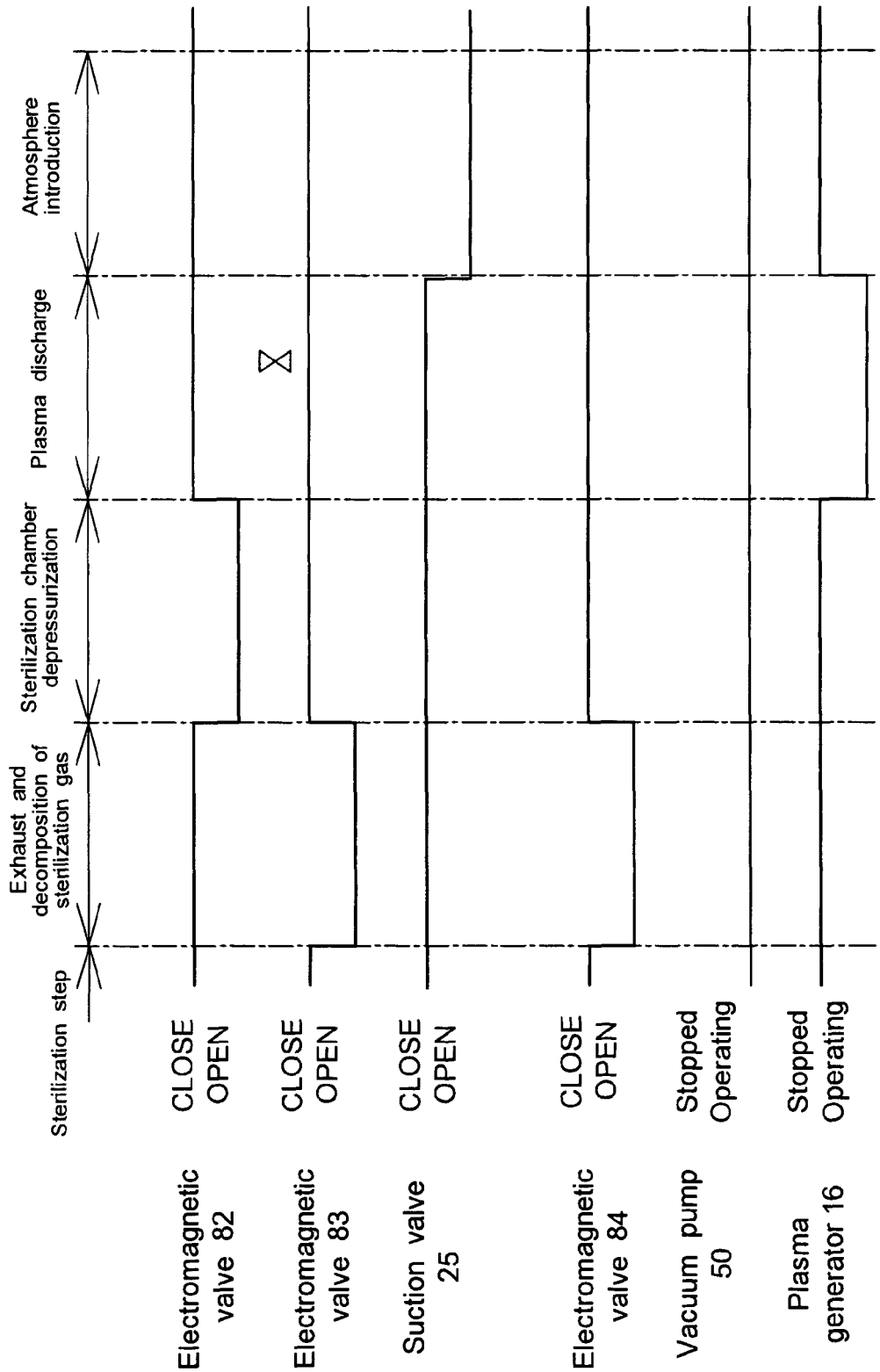
FIG. 21 is a time chart of a vacuum exhaust step.

The exhaust steps beginning with the main sterilization step are explained in detail using the time chart of FIG. 21. In the sterilization gas exhaust and decomposition step of Step S106 in the flow chart described above, electromagnetic valve 82 is closed while electromagnetic valves 83 and 84 are opened and vacuum pump 50 is operated to move sterilization gas inside chamber 1 to exhaust and decomposition line 81b via electromagnetic valve 83, so that the sterilization gas is broken down and released into the atmosphere. In the sterilization chamber depressurization step of Step 108, electromagnetic valve 83 is closed, electromagnetic valve 82 is opened, and vacuum pump 50 is operated to depressurize the inside of chamber 1. In the plasma discharge step of Step S110, electromagnetic valves 82 and 83 are closed and plasma generator 16 is turned on to generate plasma in chamber 1. In the atmosphere introduction step of Step S111, suction valve 25 of chamber 1 is opened with electromagnetic valves 82 and 83 still closed to introduce atmosphere into chamber 1.

Figure 15:
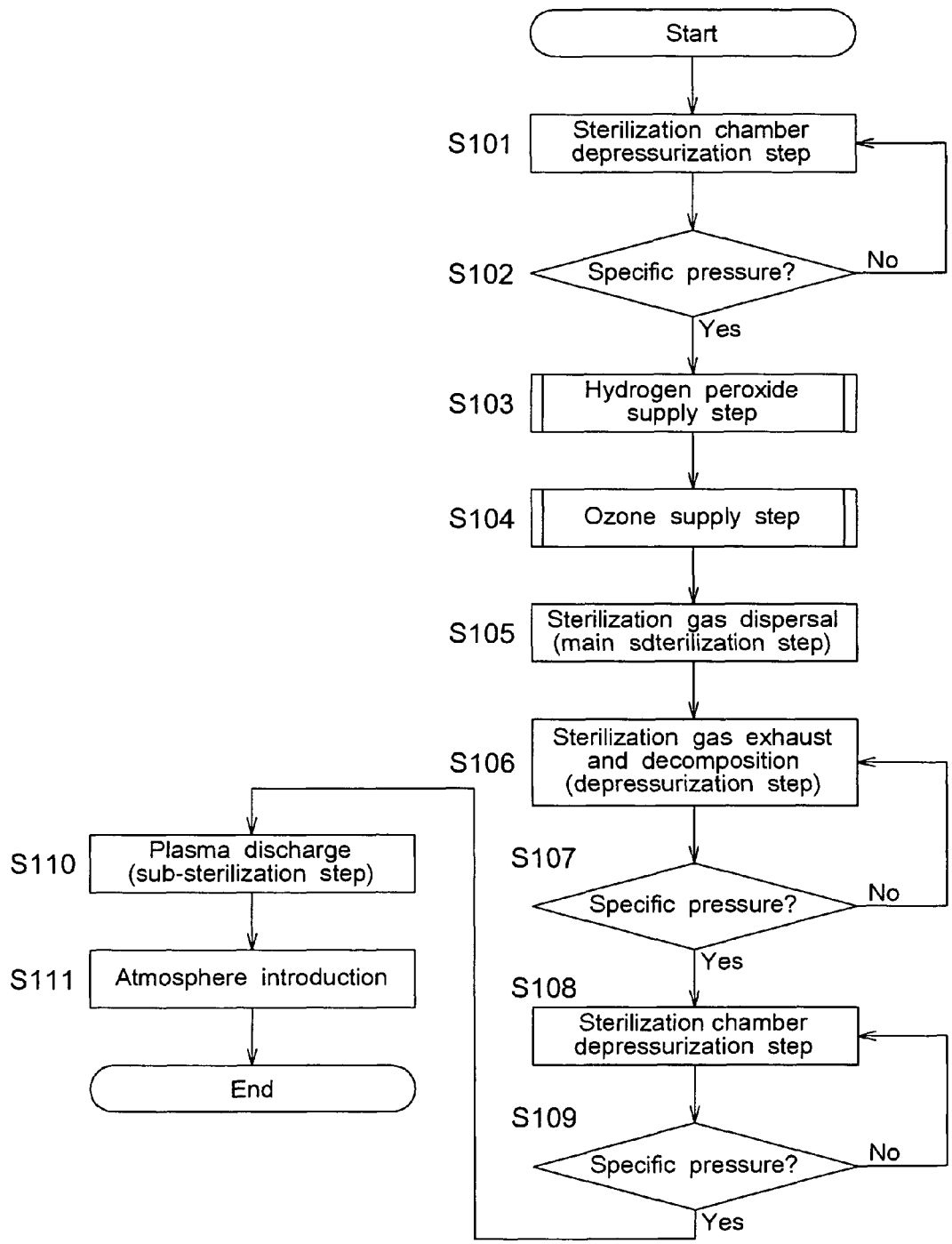
FIG. 15 is a flow chart showing the operations of a sterilization apparatus.
Figure 16:
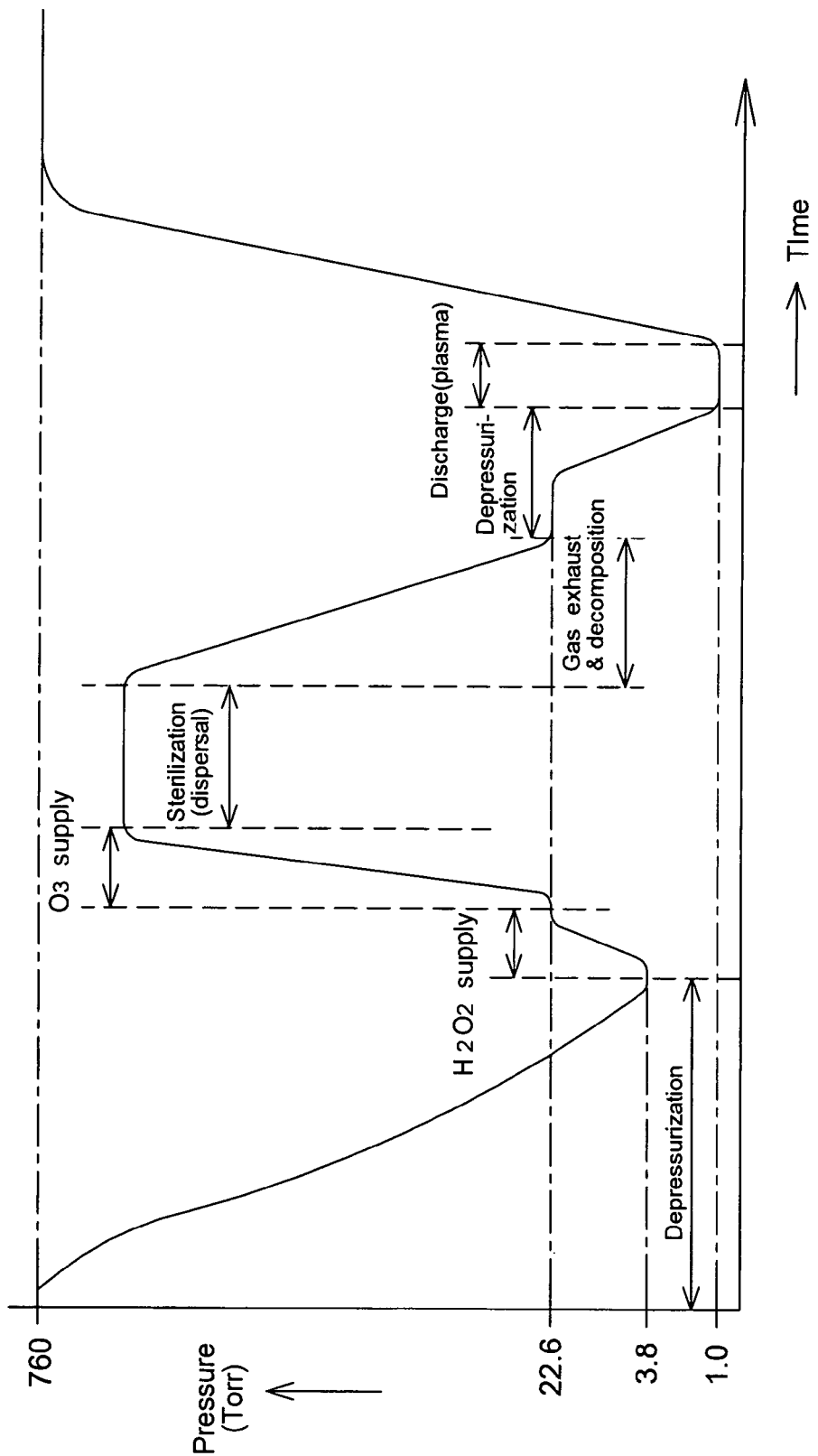
FIG. 16 shows pressure changes within a chamber.
Figure 22:
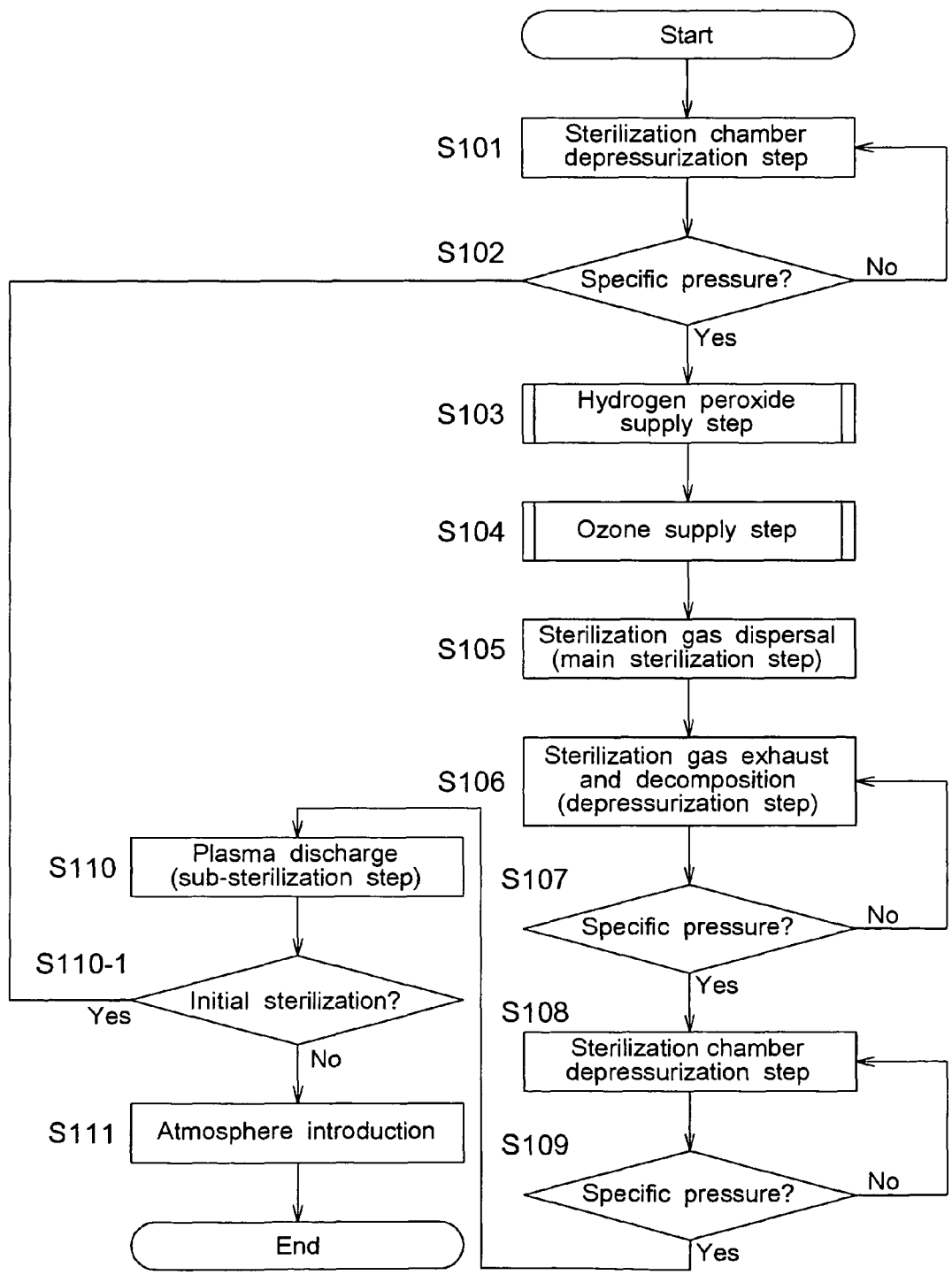
FIG. 22 is a flow chart showing the operations of a sterilization apparatus according to a modification of FIG. 15.

FIG. 22 is a modification of the flow chart of FIG. 15. A Step 110-1 of determining whether or not this sterilization is the initial sterilization is included here after completion of the sub-sterilization step of Step S110, and if it is the initial sterilization, return to Step S102, repeat sterilization, and when the second sterilization is complete go on to Step S111 and end. In this way sterilization can be repeated twice to obtain better and more reliable sterilization effects. The number of repetitions can be increased as necessary.

As shown in FIG. 23(a), in another embodiment of the hydrogen peroxide supply unit one end of ceramic heater 96, which is in the form of a pipe with a 90° bend, can be attached to the inside end of hydrogen peroxide injection pipe 95, which is attached to the wall of chamber 1, with the other end of ceramic heater 96 pointing upwards and filled with stainless wool 97. Hydrogen peroxide injected from hydrogen peroxide injection pipe 95 through electromagnetic valve 32 is heated and vaporized by ceramic heater 96, and is supplied inside chamber 1 after passing through stainless wool 97. That part of the hydrogen peroxide that has been condensed by contact with stainless wool 97 flows downward by the force of gravity along the curved part of ceramic heater 96, and is returned to the hydrogen peroxide being injected through hydrogen peroxide injection pipe 95.

Moreover, as shown in FIG. 23(b), Venturi tube 98 can be provided between chamber 1 and electromagnetic valve 76 at the outlet of ozone tank 75, with hydrogen peroxide suction pipe 100 attached via electromagnetic valve 99 to the narrow part of this Venturi tube 98 and hydrogen peroxide suction pipe 100 inserted into hydrogen peroxide tank 101 so that hydrogen peroxide can be supplied on the current of ozone supplied to chamber 1 from ozone tank 75.

In the aforementioned embodiments, hydrogen peroxide and ozone are used together for sterilization, but the user can also be allowed to select one or the other kind of sterilization by means of a switch depending on the type of object to be sterilized. For example, if the object to be sterilized is formed from cellulose, latex rubber, silicon rubber or the like, there is a risk that hydrogen peroxide may be adsorbed, hindering sterilization, so sterilization with ozone alone can be selected. When sterilizing with ozone alone, ozone is preferably injected with the humidity inside chamber 1 maintained at about 80%. This increases the sterilization effect of the ozone.

Figure 24:
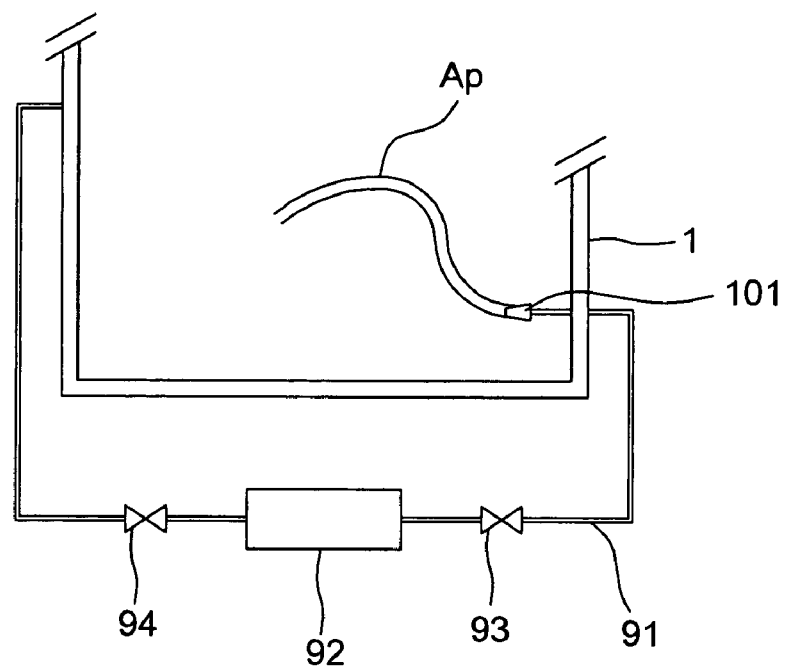
FIG. 24 shows a structure for sterilizing a tube-shaped object to be sterilized.
Figure 25:
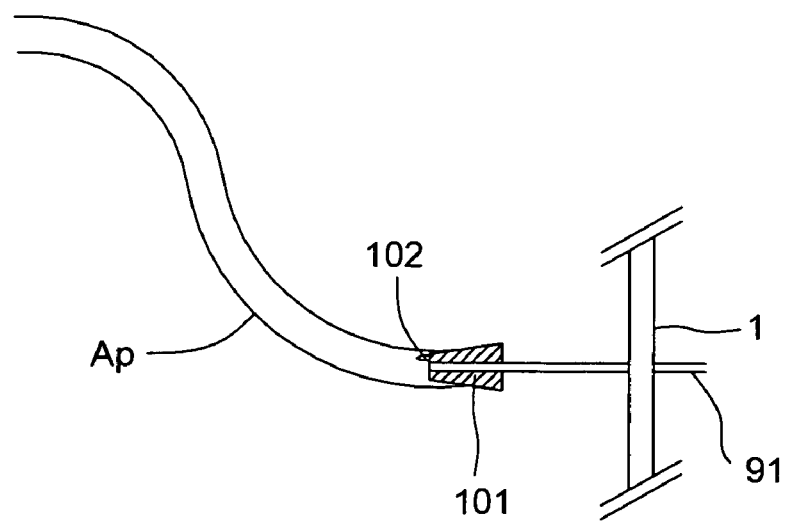
FIG. 25 is a partial enlarged view of FIG. 24.

FIGS. 24 and 25 show a structure for sterilizing a tubular object to be sterilized, such as a catheter or infusion tube. Conventionally, it has been difficult to sterilize a tubular object to be sterilized. As shown in these figures, tube adapter 101, which is made of a plastic or other insulating material, is attached within chamber 1 to the intake end of sterilization gas circulation line 91 of sterilization gas circulation unit 1A, and a tubular object to be sterilized Ap can be fitted onto the tip of this tube adapter 101. In this way, sterilization gas can be passed through the bore of object to be sterilized Ap by driving circulation pump 92, and retention of sterilization gas in the tube can be prevented. Moreover, needle electrode 102 can be attached to the end surface of tube adapter 101, and this needle electrode 102 can be connected to plasma generator 16. Plasma generator 16 can be switched so as to apply voltage to either one of high-voltage electrode 12 or this needle electrode 102. When high-frequency voltage is applied to needle electrode 102, plasma is generated within the tube, enhancing the sterilization effects.

Figure 26:
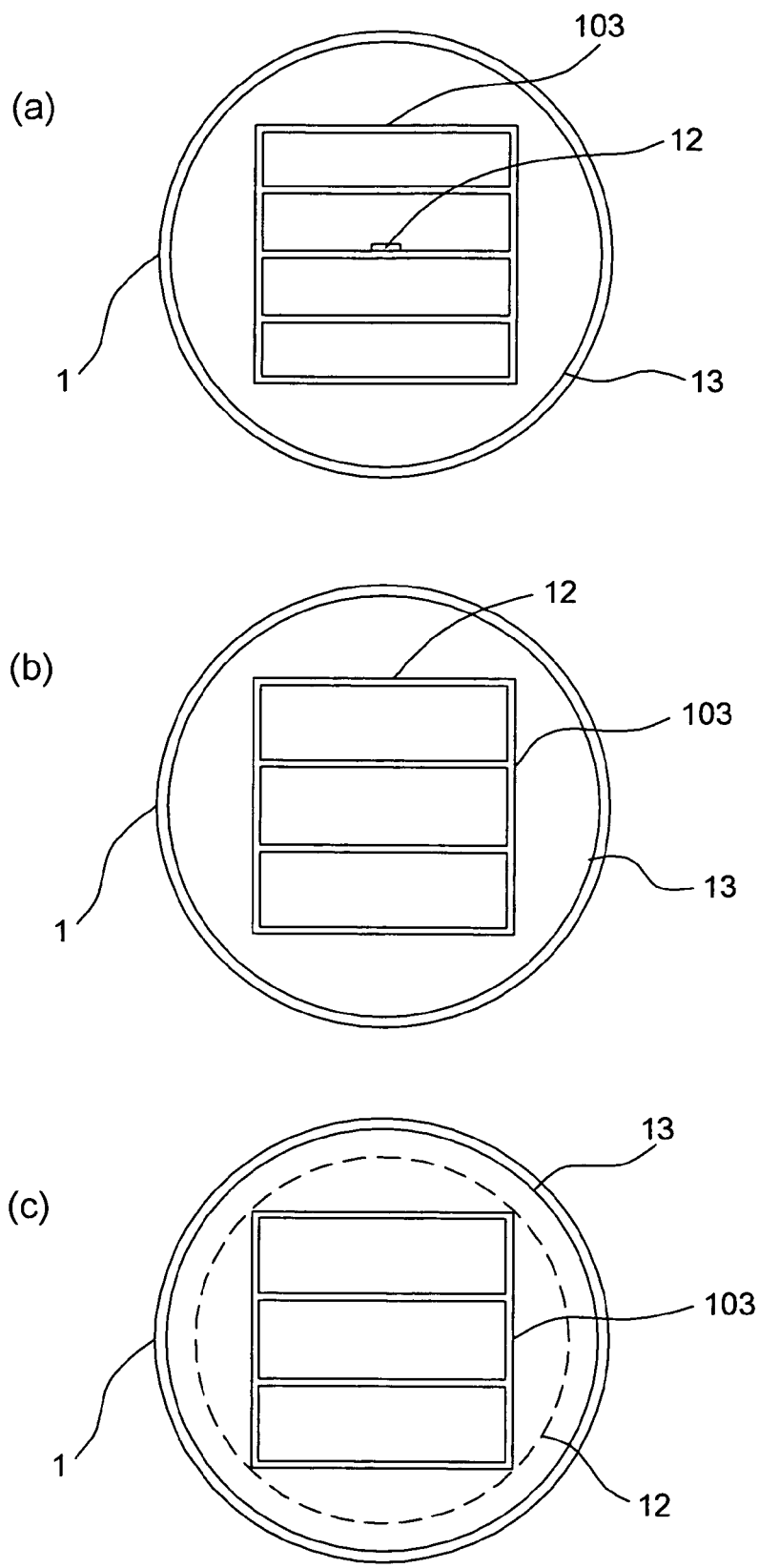
FIG. 26 shows other examples of electrodes.

FIG. 26 shows other electrode structures. In FIG. 26(a), high-voltage electrode 12 is attached to the center of rack 103, which is in the center of chamber 1 and is made of an insulating material, while low-voltage electrode 13 is arranged around the inner circumference of chamber 1. In FIG. 26(b), rack 103 itself inside chamber 1 is a high-voltage electrode formed from a conductive material, while low-voltage electrode 13 is arranged around the inner circumference of chamber 1. In FIG. 26(c), porous cylindrical high-voltage electrode 12, which consists of an electrically conductive material, is arranged along the inner circumference of chamber 1 surrounding rack 103 inside chamber 1, while low-voltage electrode 13 is arranged around the inner circumference of chamber 1. These electrode structures can also generate uniform plasma and provide adequate sterilization effects.

The invention claimed is:

1. A sterilization method for sterilizing an object to be sterilized within a chamber, the method comprising:
    a decompression step of decompressing the chamber;
    a hydrogen peroxide supply step of supplying hydrogen peroxide into the chamber after decompression;
    an ozone supply step of supplying ozone into the chamber after supplying the hydrogen peroxide and before the chamber reaches atmospheric pressure;
    a sterilization step of sterilizing the object to be sterilized by diffusing the hydrogen peroxide and ozone supplied within the chamber;

an exhaust step of exhausting gas from within the chamber after sterilization by the hydrogen peroxide and ozone; and a plasma generation step of generating plasma in a residual hydrogen peroxide and ozone atmosphere within the chamber after exhausting the gas so that hydroxy radicals generated by the plasma discharge allow the object to be sterilized.

2. The sterilization method according to claim 1, wherein said exhaust step comprises a decomposition step in which gas being exhausted from the chamber is broken down into oxygen and water.

3. The sterilization method according to claim 1, wherein said exhaust step comprises a decomposition step in which the ozone in the gas being exhausted from the chamber is broken down.

4. The sterilization method according to claim 1, wherein said sterilization step comprises a step of circulating the sterilization gas in the chamber.

* * * * *